United States Patent
Woods, Jr.

(10) Patent No.: US 6,599,707 B1
(45) Date of Patent: Jul. 29, 2003

(54) METHODS FOR IDENTIFYING HOT-SPOT RESIDUES OF BINDING PROTEINS AND SMALL COMPOUNDS THAT BIND TO THE SAME

(75) Inventor: Virgil L. Woods, Jr., San Diego, CA (US)

(73) Assignee: ExSAR Corporation, Monmouth Junction, NJ (US)

(*) Notice: Subject to any disclaimer, the term of this patent is extended or adjusted under 35 U.S.C. 154(b) by 0 days.

(21) Appl. No.: 09/393,775

(22) Filed: Sep. 10, 1999

Related U.S. Application Data

(60) Provisional application No. 60/099,847, filed on Sep. 11, 1998.

(51) Int. Cl.[7] ............. G01N 33/53; G01N 33/566; G01N 33/563; G01N 31/00; G01N 33/00
(52) U.S. Cl. ............. 435/7.1; 436/501; 436/512; 436/517; 436/2; 436/86; 436/144; 436/173
(58) Field of Search ................. 435/7.1; 436/512, 436/501, 317, 2, 86, 144, 173

(56) References Cited

U.S. PATENT DOCUMENTS

| | | | |
|---|---|---|---|
| 5,101,059 A | 3/1992 | Carpino et al. | 549/388 |
| 5,254,730 A | 10/1993 | Kilgore | 562/575 |
| 5,273,886 A | 12/1993 | Aswad | 435/15 |
| 5,470,753 A | 11/1995 | Sepetov et al. | 436/89 |
| 5,658,739 A | 8/1997 | Woods | 435/7.1 |
| 5,786,218 A | 7/1998 | Pivonka et al. | 436/34 |
| 6,291,189 B1 | 9/2001 | Woods, Jr. | 435/7.1 |

FOREIGN PATENT DOCUMENTS

| | | |
|---|---|---|
| EP | 0 529 604 A1 | 3/1993 |
| WO | WO 99/09204 A1 | 2/1999 |

OTHER PUBLICATIONS

Novotny et al., 1989, "On the attribution of binding energy in antigen–antibody complexes McPC 603, D1.3 and HyHEL–5," *Biochemistry* 28:4735–4749.

Ekiel et al., Jul. 27, 1998, "Effect Of Peptide Binding On Amide Proton Exchange Rates In The PDZ2 Domain From Human Phosphatease hPTP1E," *Biochem. Cell Biol.*, vol. 76, pp. 334–340.

Englander et al., Dec. 3, 1984, "Protein Hydrogen Exchange Studied By The Fragment Separation Method," *Analytical Biochemistry*, vol. 147, pp 234–244.

Goshe, Michael Bryan, Aug. 1999, "Hydroxyl Radical Induced Hydrogen/Deuterium Exchange: Identification Of Amino Acid Residues Involved In Peptide–Protein Interactions," PhD. Thesis, Department Of Biochemistry, Case Western University, pp 1–254.

Hilser et al., 1996, "Structure–based Calculation Of The Equilibrium Pathway Of Proteins. Correlation With Hydrogen Exchange Protection Factors," *J. Mol. Biol.*, vol. 262, pp 756–772.

Supplementary European Search Report, EP 99 94 6946, Munich, Germany, Jul. 19, 2001. pp 1–2.

Anderegg and Wagner, 1995, "Mass spectrometric characterization of a protein–ligand interaction," *J. Am. Chem. Soc.* 117:174–1377.

Englander and Englander, 1983, "Functional Labeling in Hemoglobin," In: *Structure and Dynamics: Nucleic Acids and Proteins*, Clementi and Sarma, eds. Adenine Press, NY, pp. 421–433.

Englander et al., 1983, "Identification of an Allosterically Sensitive Unfolding Unit in Hemoglobin," *J. Mol. Biol.* 169:325–344.

Milne et al., 1998, "Determinants of protein hydrogen exchange studied in equine cytochrome c," *Protein Science* 7:739–745.

Mylvaganam et al., 1998, "Structural Basis for the Binding of an Anti–cytochrome c Antibody to its Antigen: Crystal Structures of FabE8–Cytochrome c Complex to 1.8 Å Resolution and FabE8 to 2.26 Å Resoltion," *J. Mol. Biol:* 281:301–322.

Wang et al., 1997, "Hydrogen exchange/electrospray ionization mass spectrometry studies of substrate and inhibitor binding and conformational changes of Escherichia coli dihydrodipicolinate reductase," *Biochemistry* 36(13):3755–3759.

Bai et al., 1995, "Thermodynamic parameters from hydrogen exchange measurements," *Methods Enzymol.* 259:344–356.

Clackson and Wells, 1995, "A hot spot of binding energy in a hormone–receptor interface," *Science* 267:383–386.

Connelly et al., 1993, "Isotope effects in peptide group hydrogen exchange," *Proteins* 17(1):87–92.

Deng et al., 1999, "Selective Isotope Labeling Demonstrates That Hydrogen Exchange at Individual Peptide Amide Linkages Can Be Determined by Collison–Induced Dissociation Mass Spectrometry," *Journal of the American Chemical Society* 121(9):1966–1967.

Englander and Englander, 1994, "Structure and energy change in hemoglobin by hydrogen exchange labeling," *Methods Enzymol.* 232:26–42.

Goshe and Anderson, 1999, "Hydroxyl Radical–Induced Hydrogen/Deuterium Exchange in Amino Acid Carbon–Hydrogen Bonds," *Radiation Research* 151:50–58.

(List continued on next page.)

Primary Examiner—Stephanie W. Zitomer
(74) Attorney, Agent, or Firm—Pennie & Edmonds LLP

(57) ABSTRACT

The present invention provides methods of identifying hot-spot residues for one or both members of a receptor-ligand complex of interest. Further provided are methods of using receptor hot-spot residues to identify compounds that functionally bind a receptor in a manner that mimics the binding of a known ligand for the receptor.

61 Claims, No Drawings

OTHER PUBLICATIONS

Hartman et al., 1989, "Examination of the function of active site lysine 329 of ribulose–bisphosphate carboxylase/oxygenase as revealed by the proton exchange reaction," *J Biol Chem.* 264(20):11784–11789.

Kim et al., 1982, "Influence of charge on the rate of amide proton exchange" *Biochemistry* 21(1):1–5.

Loo et al., 1990, "Primary sequence information from intact proteins by electrospray ionization tandem mass spectrometry," *Science* 248(4952):201–204.

Mayne et al., 1992, "Effect of antibody binding on protein motions studied by hydrogen–exchange labeling and two–dimensional NMR," *Biochemistry* 31:10678–10685.

McCloskey, 1990, "Introduction of deuterium by exchange for measurement by mass spectrometry" *Methods Enzymol.* 193:329–38.

Molday et al., 1972, "Primary structure effects on peptide group hydrogen exchange" *Biochemistry* 11(2):150–158.

Paterson et al., 1990, "An antibody binding cite on cytochrome c defined by hydrogen exchange and two–dimensional NMR," *Science* 249:755–759.

Rogero et al., 1986, "Individual breathing reactions measured by functional labeling and hydrogen exchange methods," *Methods Enzymol.* 131:508–517.

Ross et al., 1979, "An experimental procedure for increasing the structural resolution of chemical hydrogen–exchange measurements on proteins: application to ribonuclease S peptide," *J Mol Biol.* 133(3):399–416.

Ross et al., 1982, "Effects of binding of S–peptide and 2'–cytidine monophosphate on hydrogen exchange from the S–protein component of ribonuclease S. The amide protons of serine 123 and valine 124," *J Mol Biol.* 160(3):517–530.

Rose et al., 1981, "Hydrogen exchange from identified regions of the S–protein component of ribonuclease as a function of temperature, pH, and the binding of S–peptide," *J Mol Biol.* 145(4):835–851.

Rosnack et al., 1992, "C–terminal sequencing of peptides using electrospray ionization mass spectrometry," *Rapid Commun Mass Spectrom.* 6(11):637–640.

Sepetov et al., 1993 "The use of hydrogen–deuterium exchange to facilitate peptide sequencing by electrospray tandem mass spectrometry," *Rapid Commun Mass Spectrom.* 7(1):58–62.

Smith et al., "Carboxy–terminal Protein Sequence Analysis Using Carboxypeptidase P and Electrospray Mass Spectrometry," *In: Techniques in Protein Chemistry IV*, pp. 463–470, 1993.

Smith et al., 1997, "Probing the Non–covalent Structure of Proteins by Amide Hydrogen Exchange and Mass Spectrometry," *Journal of Mass Spectrometry* 32:135–146.

Smith–Gill, 1994, "Protein epitopes: functional vs. structural definitions," *Res Immunol.* 145:67–70.

Thevenon–Emeric et al., 1992 "Determination of amide hydrogen exchange rates in peptides by mass spectrometry," *Anal Chem.* 64(20):2456–2458.

Tsugita et al., 1992, Chemistry Letters pp. 235–238.

Wells, 1996, "Hormone mimicry," *Science* 273:449–450.

Statement regarding communications between Virgil L. Woods, Jr., and personnel at Case Western Reserve University in first half of 1999.

METHODS FOR IDENTIFYING HOT-SPOT RESIDUES OF BINDING PROTEINS AND SMALL COMPOUNDS THAT BIND TO THE SAME

This application claims priority to provisional patent application entitled "Methods For Identifying Hot Spot Residues of Binding Proteins And Small Compounds that Bind to Same", Ser. No. 60/099,847, filed Sep. 11, 1998.

1. FIELD OF THE INVENTION

The present invention relates to methods of identifying hot-spot residues of a member of a receptor-ligand binding pair of interest. The invention further provides methods of using information about receptor hot-spots for a receptor-ligand pair of interest to guide the identification of compounds that functionally bind to such regions of the receptor in a manner that mimics the ligand.

2. BACKGROUND OF THE INVENTION

Protein-protein interactions such as those observed in many receptor-ligand complexes are typically mediated by large binding surfaces comprising ten to thirty contact amino acid residues on each protein of the complex (Clackson & Wells, 1995, Science 267:383–386). Recently, it has been suggested for some binding pairs that within each binding surface, the predominant contribution to the overall free energy of binding of the complex is due to only a few residues within each binding surface. (Clackson & Wells, 1995, supra).

For example, recent studies by Wells and collaborators have characterized the binding surfaces of the complex formed between human growth hormone and its cellular receptor. (Clackson & Wells, 1995, supra; Pearce et al., 1996, Biochemistry 35:10300–10307; Wells, 1996, Proc. Natl. Acad. Sci. USA 93:1–6). X-ray crystallographic studies had shown that approximately thirty amino acid side chains of the hormone contact approximately thirty amino acid side chains of the receptor. An array of mutant human growth hormone proteins and mutant receptor proteins were prepared to estimate the energetic contribution of each amino acid of the contact surface to the overall binding interaction. The study measured the binding affinities of various complexes between mutant hormones and native receptors and also between native hormones and mutant receptors.

Surprisingly, only a small number of amino acid residues within the extensive binding surfaces accounted for most of the binding energy. Overall, fewer than half of the contact residues contributed measurably to the binding interaction. Eight receptor residues and eleven hormone residues accounted for over 75% of the free energy of binding of the hormone-receptor complex. Within each group of residues on either binding pair, a limited number of "hot-spot" amino acids contributed most to the total free energy of binding. Surrounding each "hot-spot" was a group of several amino acids that contributed at lesser levels, and this group was in turn followed by a larger set of residues that contributed at even lower levels to the total free energy of binding. Most significantly, the "hot-spot" residues on the receptor binding surface directly contacted the complementary "hot-spot" amino acids on the hormone's binding surface. Subsequent studies in other systems have also shown that the total binding affinity between a receptor and a ligand is mediated mainly by small and complementary sets of "hot-spot" residues within the binding surfaces of the receptor and ligand (Wells, 1996, Science 273:449–450; Smith-Gill, 1994, Res. Immunol. 145:67–70, 1994). Some systems even suggest that multiple, non-contiguous "hot-spots" are possible.

While the methods of Wells and others can provide detailed information about residues involved in binding interactions for a variety of receptor-ligand pairs, they suffer from serious drawbacks. For example for a given receptor-binding protein pair, large panels of mutant proteins must be prepared in order to identify the thermodynamically significant or "hot-spot" residues. To do so, each residue of the receptor or ligand must be mutated individually to measure its contribution to the overall free energy of binding.

Ideally, when a three-dimensional structure of the receptor-ligand complex is available, the mutations can be limited to only those amino acids comprising the binding surfaces of each member of the pair, approximately thirty residues for each number in a typical interaction. Thus, even in such an "ideal" situation, where information about both the receptor and ligand is desired, a total of about sixty mutant proteins must be prepared (one for each residue in the binding surface of the receptor and one for each residue in the binding surface of the ligand), and the binding energy of each mutant protein for its native binding partner determined.

In a more typical situation where no three-dimensional structure is available for either binding partner, mutants must in principle be prepared for every residue of both proteins. Thus, even in an ideal situation the methods are labor-intensive and expensive. In a less than ideal situation, the time and expense of preparing the mutants and measuring binding affinities oftentimes would be comparable to that for obtaining a three-dimensional structure of the complex.

In addition, the methods do not necessarily accurately identify the hot-spot residues. Site-directed mutagenesis of individual amino acids does not simply remove an amino acid side chain from a protein. Often, mutation of a residue to, for example, an alanine, introduces local and perhaps global structural perturbations in the mutant protein. These structural changes may affect the binding interactions between the mutant protein and its ligand. As a consequence, a comparison of the binding affinities of the mutant and native proteins is unlikely to be an accurate measurement of the relative contribution that residue makes to the overall free-energy of binding. In fact, in the studies of Clackson & Wells, the sum of the apparent free energy contributions of the mutated amino acids exceeded the known free energy of binding of the native receptor-native ligand complex by a factor of two (see, Clackson & Wells, 1995, supra). Clackson & Wells concluded that the excess measured binding energy was due to mutant-induced structural changes.

Thus, it would be highly desirable to have available methods for identifying hot-spot amino acid residues for receptor-ligand pairs which do not suffer from the above-described limitations. In particular, it would be highly desirable to have available methods for identifying receptor-ligand hot-spot residues which are fast and inexpensive, and which further permit the identification of hot-spot residues for a native receptor-ligand pair without having to mutate either the receptor or ligand.

Small compounds that bind to, and thereby antagonize (antagonists) or activate (agonists) receptors of therapeutic importance are of considerable commercial value. However, to date the ability to rapidly and easily identify such small compounds, particularly those that are able to interact with protein receptors that have large polypeptide or protein ligands, is limited. In most instances, such compounds are obtained through the laborious process of rational drug design, which usually requires detailed knowledge about the three-dimensional structure of the receptor-ligand co-complex or other structure-function information. Rational drug design generally involves designing compounds based on available structure-function information on a compound-by-compound basis and screening the individual compounds in biological assays to identify those compounds which produce a desired biological activity. Usually, detailed structure-function or three-dimensional structural information for the receptor-compound complex is obtained so that the design hypotheses can be verified.

Typically, the detailed structure-function information necessary to design and assess the compounds is obtained from NMR or x-ray crystallographic studies with the receptor-ligand co-complex. Both of these technologies require large quantities of pure, co-complex, expensive, specialized equipment and highly skilled technicians, making such structural information extremely costly and time consuming to obtain. In addition, while the detailed structural information obtained from these methods can oftentimes identify those residues of each member of the binding pair that are involved in the binding interaction, neither of these methods have been used to identify the individual residues which make significant contributions to the overall free energy of binding of the receptor-ligand complex; in fact, x-ray crystallography simply cannot generate this detailed information. Moreover, to date, rational drug design methodologies have proven inadequate for designing receptor agonists, which are an increasingly important class of pharmaceutical targets. Induction of receptor activation by agonists requires more than simple receptor binding. Agonist activity usually results from receptor conformational change or receptor subunit oligomerization that is induced by ligand binding. Agonist ligands must be capable of binding to precisely the correct subregion(s) of the receptor and in the correct manner required for induction of these receptor changes. When agonists appropriately bind to receptors, a portion of the binding energy is employed to produce these receptor structural changes. Presently available structure determination technologies (x-ray crystallography, NMR) have great difficulty in identifying and localizing the parts of the receptor that participate in such ligand-induced structural changes, and in identifying the mechanisms by which they are induced by agonist binding.

Recently, "non-rational" combinatorial library methodologies have been developed, in part to ameliorate the drawbacks of rational drug design. In these non-rational methods, large libraries of compounds are synthesized and screened for the ability to bind a target receptor of interest. The structures of the identified compounds are elucidated and used as lead compounds for subsequent rounds of library synthesis and screening or as lead structures for rational drug design.

While these methods have the allure of being able to randomly or semi-rationally sample large sectors of "conformation space" in a relatively short period of time, they suffer from many drawbacks. For example, in order to identify a lead compound from a purely random library, millions, and oftentimes trillions, of compounds must be synthesized and screened. Thus, while theoretically pharmaceutical leads can be identified from a purely random library, in practice the library methods are merged with rational design methods to create "focused libraries" that have a higher probability of containing a suitable lead structure. Thus, even these library methodologies rely, to some extent, on structure-function information.

Moreover, while compounds which bind a target receptor can be identified, no information is provided about where on the receptor the compound binds. Whether the compound binds the receptor at or near the same site as the receptor's natural ligand is simply unknown. Combinatorial library methodologies are also inadequate for identifying receptor agonists for substantially the same reasons discussed above.

The ability to identify where a candidate compound of interest binds a target receptor of interest without having to obtain expensive and laborious high resolution three-dimensional structures of the receptor, ligand or receptor-ligand co-complex would be highly desirable. Of particular interest would be having the ability to identify candidate compounds which bind a receptor at the same site as the receptor's natural ligand or to identify compounds that act as receptor agonists. Current methods for achieving these goals are inadequate. Accordingly, these are objects of the present invention.

3. SUMMARY OF THE INVENTION

These and other shortcomings in the art are overcome by the present invention, which in one aspect provides a method for identifying hot-spot residues for one or both members of a receptor-ligand pair of interest. In the method of the invention, the rates of exchange between individual hydrogens of one or both members of the receptor-ligand pair and solvent hydrogens are determined for the member in both the bound and unbound states. The individual hydrogens are correlated to specific amino acid residues within the primary sequence of the member, thereby providing hydrogen exchange rates for hydrogens on specifically identified amino acid residues comprising the member. From these exchange rates, those residues which individually contribute at least about 10–20% of the overall free energy of binding of the receptor-ligand complex are identified as constituting the "hot-spot" residues for that member of the receptor-ligand pair.

The method can be used with or without the aid of three-dimensional structure or other structure-function information about the particular receptor, ligand or receptor-ligand pair. The only requirement is that the primary amino acid sequence of the binding member of interest be known.

Furthermore, in general, the method does not preclude application to finding hot-spot residues in a non-native, or mutated receptor. Such an approach could find utility in, for example, establishing structure-function relationships, particularly because mutants often have unpredictable conformational changes with respect to the native receptor.

The methods described herein provide significant advantages over currently available methodologies for identifying receptor and/or ligand hot-spot residues. For example, according to the methods of the invention, hot-spot residues can be simply, rapidly and inexpensively identified for each member of a native receptor-ligand complex. Thus, unlike the methods described in the art, which require mutation of the receptor and/or ligand, the method of the invention permits, for the first time, reliable identification of hot-spot residues of receptors and/or ligands in their truly native, biologically relevant conformations.

In another aspect, the invention provides a method for identifying compounds that interact with a target receptor of interest in a manner similar to a known ligand for that receptor; i.e., the invention provides a method of identifying compounds which act as binding mimics of known receptor ligands. According to the method of the invention, receptor hot-spot residues for a receptor-ligand pair of interest are first identified. Candidate compounds are then screened with the receptor to identify those candidate compounds that interact with at least one, and preferably at least a majority or even more, of the receptor hot-spot residues. Those candidate compounds that interact with at least one receptor hot-spot residue are selected as small molecule binding "mimics" of the known ligand.

For any given receptor-ligand pair, the receptor hot-spot residues can be determined by any of several techniques, including, for example, the methods described herein, hydrogen exchange with heavy hydrogen (deuterium or tritium) in conjunction with nuclear magnetic resonance (NMR) or mass spectroscopy, tritium exchange in conjunction with radioactivity measurements and in conjunction with site-directed mutagenesis. The precise binding interactions between the receptor and candidate compounds can also be characterized by any of these methods to identify compounds that "mimic" the essential receptor binding activity of the known ligand.

Each candidate compound may be first assayed for a particular biological activity of interest, such as the ability to bind, antagonize or agonize the receptor, to identify those candidate compounds which exhibit the desired biological activity, and then the active candidate compounds further screened to identify those that interact with a receptor hot-spot residue. Alternatively, the candidate compounds may be directly screened to identify those that interact with a receptor hot-spot residue without first assaying for biological activity.

Selection of the initial candidate compounds to be screened can be guided by a structural model of the ligand or the receptor-ligand complex, by available structure-function information for the receptor-ligand complex, or by completely random processes. The initial candidate compounds can be synthesized individually or can be synthesized using any of the well-known combinatorial library methodologies. Candidate compounds, and in particular combinatorial libraries of candidate compounds, that are first screened for biological activity, particularly binding activity, can be screened in pools in a batch-wise fashion using any of the numerous screening methods described in the art to identify biologically active compounds for further analysis according to the invention.

Ideally, the method of the invention is used iteratively to identify ligand mimics. In the iterative method, the results of one round of screening guide the selection of candidate compounds for the next round of screening. For example, the structures of candidate compounds identified in a first round of hot-spot screening can be determined and these structures used to guide the synthesis of new or modified candidate compounds. After several rounds of synthesis and screening, compounds are identified that precisely mimic the known ligand; i.e., compounds are identified that precisely interact with those receptor hot-spot residues contacted by the known ligand.

The methods of the invention for identifying compounds which bind a receptor provide significant advantages over currently available techniques. Because the preferred methods utilize sensitive hydrogens on the amino acid side-chain or backbone as reporters of local changes in environment, the methods are able to identify compounds that interact with a target receptor of interest at the most biologically significant residues–those receptor residues that contribute most to binding the receptor's natural ligand. Quite significantly, the methods do not require detailed structure-function or three-dimensional structural information for the receptor, ligand, receptor-ligand co-complex or receptor-compound co-complex, though interpretation of results is enhanced by the availability of such information. The only requirement is that the primary amino acid sequence of the receptor of interest be known. Thus, the methods of the invention permit the identification of "ligand mimics", particularly small compound ligand mimics of the essential binding function of the natural ligand, with unprecedented ease.

Moreover, the methods provide insights into the nature of the ligand-binding induced receptor structural changes required for agonist activity. This, combined with the ability to focus small molecule design to known ligand-defined hot-spots allows ready identification of compounds that function as receptor agonists–a feat that is simply unprecedented in the art.

Thus, in a final aspect the invention provides methods of identifying compounds, particularly small organic compounds, which act as agonists for a target receptor of interest. According to the method of the invention, hydrogen exchange techniques as previously described are used to identify three distinct classes of receptor amino acid residues for a receptor-agonist pair of interest:

(i) those that reside in the receptor-agonist binding surface;

(ii) those that participate in conformational changes as a consequence of receptor-agonist binding; and (iii) that participate in binding-induced receptor sub-unit oligomerization. The receptor is then screened with candidate compounds using the hydrogen exchange techniques described herein to identify those which interact with at least one receptor amino acid residue from class (ii) or (iii), above. The candidate compound is considered to interact with one of these receptor residues if the receptor residue has a protection factor of at least one upon formation of a receptor-candidate compound complex. The candidate compounds may be screened for biological activity prior to screening in the methods of the invention, as previously described.

The methods may be used iteratively in a manner similar to that described above to identify compounds which interact with a majority of the receptor amino acid residues of class (ii) or (iii).

3. DEFINITIONS

As used herein, the following terms shall have the following meanings:

"Ligand:" refers to any molecule which is capable of binding a receptor. The ligand may be a small organic compound, or a large molecule such as a polypeptide or protein.

"Receptor:" refers to any molecule capable of binding a ligand. Thus, as used herein receptor refers not only to molecules generally recognized as belonging to the class of binding molecules designated as "receptors," such as, for example, receptors for cytokines, growth factors, chemokines, hormone receptors, adhesion receptors, apoptosis receptors, etc., but is also intended to include any molecule which can bind another molecule, including for example, an antibody or an enzyme.

The receptor may be identical in primary amino acid sequence to a naturally occurring receptor, or it may be a functionally active fragment, mutant or derivative thereof. The fragment, mutant or derivative may have the same or different binding or other biological characteristics relative to the parental protein.

Receptors of particular interest include integral membrane proteins, as they are difficult to crystallize for study by X-ray diffraction. Receptors too large to study by NMR methods, e.g., those larger than about 50 kDa, are also of special interest, particularly if they cannot be characterized as a composite of two or more separately analyzable domains. Examples of receptors of particular interest include integrins (which are large integral membrane proteins), cell surface receptors for growth factors (including cytokine receptors), "seven-spanners," selectin, and cell surface receptors of the immunoglobin superfamily (e.g., ICAM-1).

As will be appreciated by those of skill in the art, the designation of "receptor" and "ligand" is somewhat arbitrary. Typically the term "receptor" is conferred upon the larger of the two binding partners, or upon the member of the binding pair which is a protein. For purposes of the present invention, the expressions "receptor" and "ligand" do not carry such limitations; they merely each refer to one member of a pair of binding molecules.

"Protein:" as used herein includes, mutatis mutandis, polypeptides, oligopeptides and derivatives thereof, including, by way of example and not limitation, glycoproteins, lipoproteins, phosphoproteins and metalloproteins. The essential requirement for a molecule to be considered a protein is that it feature one or more peptide (—HNC(O)—) bonds, as the amide hydrogen of the peptide bond (as well as those on the side chains of certain amino acid residues) has certain properties which permit it to be analyzed by hydrogen exchange.

"Agonist:" as used herein refers to a ligand that, upon binding to a receptor, triggers activation of a chemical signaling cascade that results in a definable change in the behavior or physical or biological state of a cell.

"Antagonist:" as used herein refers to a molecule that, by virtue of binding to a receptor or agonist, is able to block the cell-activating influence of the agonist, and which itself does not result in substantial activation of the cell.

"Labile Hydrogen:" is a general description of any hydrogen that may be exchanged with a solvent hydrogen under the conditions of the exchange experiment. One category of such hydrogens is the amide hydrogens found on the protein or peptide backbone. Exchange of these hydrogens, as described herein, is referred to as "amide hydrogen exchange". Another category comprises hydrogens bound to any carbon on the amino acids comprising the protein, including backbone and side chains that may temporarily be rendered labile under specific experimental conditions. Exchange of these hydrogens, as described herein, is referred to as "alkyl hydrogen exchange."

"Conditions of Slowed Hydrogen Exchange:" refers to conditions in which the rate of labile hydrogen exchange at residue atoms freely exposed to solvent is reduced substantially, i.e., enough to perform the various manipulations necessary to handle the samples without undue or unacceptable loss of solvent-exposed labile hydrogens.

Conditions of slowed alkyl hydrogen exchange are easily, almost trivially achieved as alkyl exchange occurs only when particular experimental conditions temporarily induce it.

Amide hydrogen exchange, however, is always occurring, to some extent, with a rate that is a function of factors including temperature, pH and solvent composition. The rate is decreased three fold for each 10° C. drop in temperature. Hence use of temperatures close to 0° C. is preferred. In water, the minimum amide hydrogen exchange rate is at a pH of 2–3. As conditions diverge from the optimum pH, the amide hydrogen exchange rate increases, typically by 10-fold per pH unit increase or decrease away from the minimum. Use of high concentrations of a polar, organic cosolvent shifts the pH minimum to higher pH, potentially as high as pH 6 and perhaps, with the right solvent, or even higher.

By way of example, at pH 2.7 and 0° C., the typical half life of a tritium or deuterium label at an amide position freely exposed to solvent water is about 70 minutes. Preferably, the slowed conditions of the present inventions result in a half-life for a freely exposed amide hydrogen of at least 10 minutes, more preferably at least 60 minutes.

4. DETAILED DESCRIPTION OF THE INVENTION

4.1 INTRODUCTION

Many biological processes are mediated by noncovalent binding interactions between receptors and ligands. The identification of the structural features of the receptor and ligand which immediately contribute to those binding interactions would be useful, inter alia, in understanding the mechanisms by which drugs bind to and activate receptors and in designing or identifying drugs which alter these processes.

When both the receptor and ligand are proteins, the binding site of the pair may include as many as thirty amino acid residues on the receptor and an equal number on the ligand. These residues constitute the "binding surfaces" of the respective members of the pair. However, the individual amino acid residues of the respective binding surfaces do not necessarily contribute equally to the free energy of binding of the complex. According to the studies of Wells and others discussed in the Background section, binding is at times and perhaps usually mediated through complementary "hot-spot" regions of a small number of amino acid residues on the binding surfaces of each binding partner. Each of these "hot-spot" residues make a significant contribution to the free energy of binding, and in sum these relatively few residues can contribute as much as 40–50% of the free energy of binding of the complex. The hot-spot residues are surrounded by residues that contribute to the free energy of binding at lesser levels, and these residues are in turn surrounded by residues that contribute at even lower levels.

As used herein, the term "hot-spot residue" is intended to include those residues of a receptor or ligand binding surface that individually contribute at least about 10% of the overall free energy of binding of the receptor-ligand complex. Preferably, each hot spot residue contributes about 20 to 30%, or even more, of the free energy of binding. In sum, the hot-spot residues comprise a binding hot-spot for the receptor or ligand. Each binding surface may have a single hot-spot, or may have multiple contiguous or non-contiguous hot-spots.

Generally, the hot-spot residues in toto will constitute at least about 30%, preferably about 40%, and even more preferably 50% or more of the overall free-energy of binding of the receptor-ligand complex.

Those of skill in the art will recognize that in many instances a ligand for a receptor may be a small polypeptide, or even a small organic molecule. In these situations, the receptor and/or ligand may not have a "binding surface". Indeed, in many of these instances, particularly those involving small ligands, only relatively few receptor amino acids might interact with the ligand. However, despite the lack of a true "binding surface", in these instances receptor and/or ligand hot-spot residues are as previously defined.

Hot-spot residues for the binding member of interest, which may be either the receptor, ligand or both, are identified according to the methods of the invention by determining the hydrogen exchange rates of the individual labile hydrogens of the member in both the bound and unbound states, and correlating these measured exchange rates with contributions to the free energy of binding of the receptor-ligand complex. Because the exchange rates can be measured for a native receptor and/or native ligand under native, biologically relevant buffer conditions, the method of the invention permits, for the first time, the identification of hot-spot residues of a native receptor or native ligand in its biologically relevant conformation.

Hydrogen exchange reflects the fact that many hydrogens in a macromolecule interchange or exchange with aqueous solvent hydrogens. Acidic hydrogens (O—H, N—H, S—H) readily exchange with aqueous solvent hydrogens under almost all physical and chemical conditions. Most acidic hydrogens exchange too rapidly with solvent hydrogen to be experimentally useful. By contrast, the more slowly exchanging peptide amide hydrogen exchanges slowly enough to be followed and measured. When contained within a polypeptide chain, every amino acid, whether gene-encoded or non-encoded, contains a peptide amide bond hydrogen, except for proline. Alkyl hydrogens (C—H) almost never exchange with aqueous solvent hydrogens except under specialised conditions and only then as long as the conditions persist. Alkyl hydrogen exchange can be induced by use of free radical generating agents including irradiation.

The measured exchange rate of a particular polypeptide labile hydrogen is directly related to the ease with which solvent water can gain close (atomic) proximity to the particular hydrogen, which is, in turn, dependent on the region of the polypeptide containing that labile hydrogen. Thus, measurement of the labile hydrogen exchange rates allow those hydrogens to be used as "sensors" or "reporters" of changes in the local environment surrounding any particular labile hydrogen. For example, in a system where a protein can be found in one of two allosteric states, the change in free energy of the local environment of a particular labile hydrogen when the protein switches between the two allosteric states is given by the formula:

$$\Delta\Delta G_i = -RT \ln(k_{i1}/k_{i2}) \quad \text{Equation (I)}$$

where $\Delta\Delta G_i$ is the change in free energy in the environment of the $i^{th}$ labile hydrogen when the protein switches from allosteric state 1 to allosteric state 2; R is the universal gas constant; T is the absolute temperature of the protein; ln is the natural logarithm; $k_{i1}$ is the exchange rate constant for the $i^{th}$ peptide labile hydrogen in allosteric state 1; and $k_{i2}$ is the exchange rate constant for the $i^{th}$ peptide labile hydrogen in allosteric state 2 (see, e.g., Englander & Englander, 1994, Meth. Enzymol. 232:26–42; Bai et al., 1995, Meth. Enzymol. 259:344–356).

The atomic and molecular forces which determine polypeptide folding and conformational changes are identical to those that determine how two different proteins bind one another. Receptor-ligand binding surfaces are comparable to cross-sections through a single folded protein, with hydrophobic residues on the inside and hydrophilic residues on the outside. The receptor-ligand binding surface is held together by hot-spot residues. Around these hot-spots, the binding surface undergoes transient localized openings that expose parts of the surface to solvent. The differing protection factors for the several contact residues reflects their differential accessibility to solvent water in the flexible receptor-ligand surface.

Given the foregoing, a similar relationship applies to local changes in free energy upon formation of a receptor-ligand complex. In this instance, the ratio of the hydrogen exchange rate in the bound and unbound states for a particular labile hydrogen, or "protection factor" for that labile hydrogen, reflects the magnitude of the exchange slowing that labile hydrogen experienced upon formation of the receptor-ligand complex. The protection factor is related to the change in free energy between the bound and the unbound states at the location of that labile hydrogen in the receptor or ligand according to Equation (II):

$$\Delta\Delta G_i = -RT \ln(PF) \quad \text{Equation (II)}$$

where $\Delta\Delta G_i$ is the change in free energy in the environment of the $i^{th}$ labile hydrogen upon formation of the receptor-ligand complex; "PF" or "protection factor" is the ratio of the exchange rates for the $i^{th}$ peptide labile hydrogen in the bound and unbound states; and the other terms are as in Equation (I).

Equation (II) allows the free-energy contribution of each residue of the receptor to the overall free energy of binding to be determined. If every amino acid residue of a receptor's binding surface contributes equally to ligand binding (and vice versa), then the labile hydrogens at each residue of the binding surface would experience identical protection factors upon ligand binding. If, however, some residues of a binding surface are more important than others to binding, then the protection factors are not identical for each residue, and the labile hydrogens at the more contributory residues have protection factors that are higher than the average. Those residues with protection factors that are greater than the per residue average for the residues within the binding surface are the "hot-spot" residues of the invention.

Unlike an unfolding polypeptide, a receptor-ligand pair can completely dissociate. As a consequence, the fraction of time the receptor and ligand spend as a complex is a function of their concentrations in solution. In contrast, the folding behavior and the consequent labile hydrogen exchange rates of a single polypeptide is essentially independent of polypeptide concentration. The dissociative behavior of a receptor-ligand complex places an upper limit on the maximum protection factor that can be measured by the hydrogen exchange technique. Assuming equimolar amounts of receptor and ligand and a monovalent receptor-ligand complex, the maximum measurable protection factor is given by Equation (III):

$$MPF = ([R-L]/K_d)^{1/2} \quad \text{Equation (III)}$$

where MPF is the maximum protection factor; [R-L] is the concentration of the receptor-ligand complex; and $K_d$ is the dissociation constant of the receptor-ligand complex (Mayne et al., Biochemistry 31:10678–10685, 1992; Paterson et al., Science 249: 755–759, 1990). All protection factors in a binding surface that are above the MPF will be measured as being equal to the MPF. Under the conditions usually employed in this technique, the maximum protection factor measurable in a binding interaction system with a $K_d$ of $1\times10^{-9}$ is 316; in a system with a $K_d$ of $1\times10^{-8}$ the MPF is 100, and in a system with a $K_d$ of $1\times10^{-7}$ the MPF is 31. If the affinity interaction is too low, hot-spot residues will not be distinguishable from less energetic regions of the binding surface. For a low affinity interaction, the concentration of the receptor and the ligand should be as high as possible. Additionally, many low-affinity biological interactions are multivalent, thereby increasing the MPF for the system.

Thus, according to the methods of the invention, hot-spot residues for one or both members of a particular receptor-ligand pair of interest are identified by obtaining the protection factors for each of the individual amino acid residues composing the respective receptor or ligand binding member and identifying those which contribute the requisite amount to the overall free energy of binding according to Equation (II).

As will be recognized from the above discussion, the methods of the invention rely on the recognition that labile hydrogen exchange rates in a polypeptide act as sensitive reporters or sensors of local changes in the environment surrounding that particular labile hydrogen, and that those labile hydrogens which experience the greatest changes in exchange rates upon formation of a receptor-ligand complex reside in a region of the binding member that is thermodynamically more significant to the overall binding interaction than others. In this sense the labelling may be called "differential labelling" because the extent of labelling of a particular site will be dependent upon its exposed (solvent accessible) surface area. Thus, while the expression "hot-spot residue" is used throughout the text to denote those amino acid residues in a receptor or ligand whose labile hydrogen has experienced a certain degree of change in solvent exchange rate upon formation of a receptor-ligand complex, the expression is not intended to imply that the particular labile hydrogen itself, or the side chain of that residue, is necessarily involved in the binding interaction. The expression is merely used as a matter of convenience to identify those residues within the primary amino acid sequence of the receptor or ligand that reside in regions of the receptor or ligand that are in close proximity to thermodynamically significant binding interactions.

In order to determine the protection factors of the individual labile hydrogens of the member of interest, the hydrogen exchange rates of the individual labile hydrogens of the member in both the bound and unbound states must be determined.

In summary, measurement of receptor-ligand binding interaction exchange rates and protection factors for labile hydrogens, and, therefore, deduction of binding hotspots, requires:

1. An initial differential labelling, by hydrogen exchange, of the receptor and ligand at labile positions with heavy hydrogen isotopes in both the bound and unbound states.

2. Localisation and quantification of the heavy hydrogen label that has been attached to the receptor and ligand in both bound and unbound states.

The foregoing differential labelling and subsequent localisation and quantification steps can, with employment of appropriate experimental methodologies, be targeted to either amide hydrogens or alkyl hydrogens.

4.1 Differential Hydrogen Exchange Labelling of Receptor and/or Ligand 4.1.1 Amide Hydrogens in the Unbound State For the unbound state, the individual amide hydrogen exchange rates can be measured during "off-exchange" or "on-exchange", or "on" then "off exchange" of heavy hydrogen using a variety of techniques. For example, exchange rates can be conveniently measured during on-exchange using conventional nuclear magnetic resonance (NMR) techniques, such as the techniques described in Cavanaugh et al., 1996, Protein NMR Spectroscopy Principles and Practice, Academic Press, New York, N.Y. In such an experiment, the member is contacted with a solution of deuterium or tritium ("heavy hydrogen"), preferably deuterium, under native conditions (typically conditions of physiological temperature, pH, ionic strength and buffer) and the rate of extinction of the amide hydrogen resonances followed by $^1$H NMR. Alternatively, the member can be on-exchanged as a function of time and the quantities and locations of label determined according to the method described below.

For measurements during off-exchange, the member must first be labeled (on-exchanged) with deuterium or tritium by contacting the member with a solution of heavy hydrogen under the desired buffer conditions, preferably under conditions wherein the receptor adopts its native conformation, such as conditions of physiological temperature, pH, ionic strength, and presence of buffer salts. During this incubation period, heavy hydrogens from the solvent exchange with solvent-accessible peptide amide hydrogens, thereby "on-exchanging" into the peptide residues of solvent-accessible portions of the member, including, among others, the peptide residues on the member's binding surface.

In some embodiments, the member is on-exchanged for a period of time sufficient to saturate the member with heavy hydrogen, i.e., for a period of time sufficient to label at least about 90%, and preferably about 95%, 96%, 97%, 98% or 99% or even more, of the amide hydrogens with heavy hydrogen. Typically, on-exchange periods on the order of a few to 24 hrs. when conducted at room or physiological temperatures and under physiological buffer and pH conditions (for example, 0.15mM NaCl, 10 mM $PO_4$, pH 7.4; "PBS") are sufficient to saturate-label the member. Identification of an appropriate on-exchange period is within the capabilities of skilled workers. Preferably, the on-exchange is performed with small incubation volumes (0.1–10 $\mu$l) and high concentrations of the member (10–100 mg/ml). However, as will be discussed in more detail below, in other embodiments the member is on-exchanged as a function of time, typically by dispensing the member into a plurality of aliquots and on-exchanging the member in each aliquot for a different period of time or by removing aliquots from an on-exchanging sample at specified periods of time.

The on-exchanged member is then contacted with a solution of normal hydrogen under the same conditions of temperature, pH, ionic strength and buffer salts used for the on-exchange. Heavy hydrogens in solvent-accessible regions of the labeled member exchange with normal hydrogens in the solvent, thereby "off-exchanging" from the member residues at rates that depend on the solvent-accessibility of the residues.

The exchange rates of the individual amide hydrogens during the off-exchange period are measured using any of a variety of available techniques. For example, if the receptor or ligand is labeled with tritium, the rates of extinction of $^3$H NMR signals can be monitored and correlated to labile hydrogen exchange rates as previously described. Conversely, the build-up rates of $^1$H NMR signals can be monitored. Similar measurements could be made with a deuterium-labeled receptor or ligand.

Alternatively, the individual amide hydrogen exchange rates can be determined by quantifying the amount of heavy hydrogen at each residue in the labeled member as a function of off-exchange time. In this embodiment, the receptor is first on-exchanged to saturation as described above and off-exchanged as a function of time, typically by dispensing the on-exchanged member into a plurality of aliquots and off-exchanging each aliquot for a different period of time or by removing aliquots from an off-exchanging member at specified time points. Typical time points are 1, 10, 100, $10^3$, $10^4$ sec., etc. Of course, the actual times used may vary, and may be experimentally determined for each system under study.

The off-exchange is quenched by changing the buffer conditions of the aliquots to conditions of slow amide hydrogen exchange, such as, for example pH 2.7 and 0° C. The locations and quantities of the heavy hydrogens are then determined for the member in each aliquot (time point) and this data analyzed using standard mathematical techniques to yield the exchange rates of the individual labile hydrogens of the member.

4.1.2 Alkyl Hydrogen Exchange Labelling in the Unbound State

In a preferred embodiment, the hydrogen studied can be an alkyl hydrogen temporarily rendered labile by free radical mediated exchange with carbon bound hydrogens within any portion of the side chain or backbone of any amino acid residue in the receptor or ligand. The mechanism by which exchange of such hydrogens is achieved is more complicated than the acid (H+) or base (OH−) catalysed amide exchange previously described. It is necessary to generate a potent hydrogen abstractor, in situ, to transiently "remove" hydrogens from the receptor carbon atoms. It is also necessary to ensure that a source of heavy hydrogen (typically heavy water), and exchange catalyst is present that can replace the abstracted hydrogen (using solvent heavy hydrogen) and, in effect, repair the protein residue whose hydrogen had been removed. Exchange: Identification of Amino Acid Residues Involved in Peptide Protein Interactions", Ph.D. Thesis, Case Western Reserve University, Ohio, 1999; M. B. Goshe and V. E. Anderson, "Hydroxyl Radical-Induced Hydrogen/Deuterium Exchange in Amino Acid Carbon-Hydrogen Bonds", Radiation Research, 151, 50–58, (1999); M. B. Goshe and V. E. Anderson, "Examining Hydroxyl Radical Induced Hydrogen/Deuterium Exchange Into Peptides: Identification of Isotopically Modified Amino Acid Residues Using ESI-MS", American Society for Mass Spectrometry, Annual Meeting, 1998.) As such, this mechanism may be finely controlled, in terms of the duration of irradiation (quantity or rate of hydroxyl radical generation), exchange facilitators (dithiothreitol, see below) and factors that minimize adverse reactions (dinitrogen oxide). The amount of receptor or ligand and the amount of radiation must be titrated such that an amount of hydrogen exchanged product sufficient to In the preferred embodiment, the hydrogen atom abstractor is the hydroxyl radical and this is generated in situ by temporary application of radiolysis, for example by γ-rays from $^{137}$Cs. (See, for example, M. B. Goshe, "Hydroxyl Radical Induced Hydrogen/Deuterium Exchange: Identification of Amino Acid Residues Involved in Peptide Protein Interactions", Ph.D. Thesis, Case Western Reserve University, Ohio, 1999; M. B. Goshe and V. E. Anderson, "Hydroxyl Radical-Induced Hydrogen/Deuterium Exchange in Amino Acid Carbon-Hydrogen Bonds", Radiation Research, 151, 50–58, (1999); M. B. Goshe and V. E. Anderson, "Examining Hydroxyl Radical Induced Hydrogen/Deuterium Exchange Into Peptides: Identification of Isotopically Modified Amino Acid Residues Using ESI-MS", American Society for Mass Spectrometry, Annual Meeting, 1998.) As such, this mechanism may be finely controlled, in terms of the duration of irradiation (quantity or rate of hydroxyl radical generation), exchange facilitators (dithiothreitol, see below) and factors that minimize adverse reactions (dinitrogen oxide). The amount of receptor or ligand and the amount of radiation must be titrated such that an amount of hydrogen exchanged product sufficient to give rise to a measurable signal in a mass spectrometer is produced. In practice, preliminary limited trial and error titration study is required for each sample of interest. Prior to irradiation, dissolved oxygen gas is removed from the solution by bubbling dinitrogen oxide gas through it. Dinitrogen oxide performs a dual function in that it also scavenges free electrons that arise from the irradiation. Upon radiolysis, or by some other means, hydroxyl radicals are generated in a concentration of, typically, 10 mM. The hydroxyl radicals which are formed are highly reactive and abstract a hydrogen atom from the nearest carbon-hydrogen bond they can contact at the atomic level (a van der Waals radius). In practice such bonds are predominantly those found in amino acid residues when they are solvent accessible. Once a hydrogen atom has been removed, a carbon-centred radical remains. In order to ensure that the spare bonding position on this carbon becomes occupied by a heavy hydrogen, the receptor and/or ligand is present, at the time of irradiation, in a solution substantially enriched with the heavy hydrogen form of water. Furthermore, a heavy hydrogen donor, such as dithiothreitol (DTT), is simultaneously present in the solution where it, in effect, catalyses the exchange reaction. When DTT is used, the pH of the solution should be below 9.0. Due to the desire to obtain the greatest amount of heavy hydrogen exchanged product as possible, the heavy water should be present in high concentration, up to 80% mole fraction for deuterium and a specific activity of 50–100 Curies/milliliter for tritiated water. Once sufficient exchange has occurred as to allow subsequent measurement, irradiation is terminated, stopping further exchange and stopping undesirable side reactions.

In amide hydrogen exchange, labelling of receptor and/or ligand by on- and off-exchange either individually or sequentially can be experimentally useful. However, only on-exchange in heavy hydrogen containing buffers is useful in alkyl hydrogen exchange labelling. This is because it is anticipated that the experimental efficiency of alkyl exchange is substantially less than amide exchange, and the heavy hydrogen signals remaining after sequential on and off alkyl hydrogen exchange would be so low as to be useless. Consequently, in order to obtain exchange rates for alkyl hydrogens, one obtains only a timed series of on-exchanged samples of receptor.

Whereas with amide hydrogen exchange rate and protection factor determination, the time of on-exchange in solution is the critical independent variable, the variable important in determining alkyl exchange rates and protection factors is the irradiation time. Such irradiation times cannot be unduly long because there is the risk of damage to the receptor or ligand sample by undesirable radiation-induced reactions such as covalent cross-linking or formation of oxidation adducts. (Putting in simple terms, there is no concept of "saturation labelling" for alkyl hydrogen exchange because the time that would be required to achieve that is long enough to substantially degrade the receptor structure through side reactions.) Irradiation is best carried out for a period of time, sufficient to produce a reliable heavy hydrogen signal, as determined by preliminary titration experiments. In particular, one may wish to focus attention, and therefore such titration studies, on a particular residue or side-chain alkyl hydrogen(s) of interest.

Typical irradiation times may comprise a sequence such as 1 minute, 10 minutes, 100 minutes. After the longest of these times, degradation of the protein structure may be sufficiently severe that one is only effectively going to obtain a lower limit on a protection factor. After irradiation, one carries out affinity chromatography on the products.

4.2 Localisation and Quantification of Exchanged Heavy Hydrogen Attached to Receptor or Ligand The locations and quantities of the heavy hydrogens attached to the receptor or ligand by either amide or alkyl exchange can be determined using a variety of techniques, such as enzymatic and/or chemical decomposition followed by NMR analysis or radiation measurement or by mass spectrometry.

In the case of amide hydrogens, this is difficult because amide hydrogens are so labile that under many conditions they exchange with one another. Consequently, degradation of a receptor or ligand whose amide hydrogens have been labelled must be carried out in such a way that the labels do not move. By contrast, alkyl hydrogens are sufficiently unreactive (in the absence of free radical generating conditions) that, once a receptor and/or ligand has been labelled by attaching heavy hydrogens to carbon atoms, the labelled structure is stable to further change.

4.2.1 Localisation of Amide Hydrogens by Enzymatic Decomposition

In one embodiment, the quantities and locations of heavy hydrogens for each aliquot or time point are determined using the controlled sequential degradation methods described in U.S. Pat. No. 5,658,739, application Ser. No. 08/919,187 filed Aug. 19, 1997, now issued as U.S. Pat. 6,291,189 B1, Sep. 18, 2001, and/or WO 97/41436, each of which is incorporated herein by reference.

Briefly, in this embodiment, which has been developed for the special case of amide hydrogen exchange, the member is shifted to conditions of slowed hydrogen exchange, conditions which optionally simultaneously denature the member. The member is then cleaved into fragments of about 5–25 amino acids in length using any method amenable to conditions of slowed hydrogen exchange. Typical methods include, for example, chemicals such as CNBr or acid stable proteolytic enzymes such as pepsin, Newlase, Aspergillus proteases, and protease type XIII, and mixtures thereof. Preferably, the member is fragmented with pepsin (10 mg/ml, covalently coupled to a solid support matrix such as Agarose or Poros® media (AL-20); at 0° C., pH 2.7, 0.1–20 min., preferably 10 min.)

The fragments are then separated from one another under conditions of slowed hydrogen exchange, for example by HPLC, and the labeled fragments identified, typically by radioactivity measurements, mass spectrometry or NMR (depending on the label) and isolated.

Each isolated labeled fragment is then sequentially degraded with, for example, carboxypeptidases, again under conditions of slow hydrogen exchange, to yield a series of subfragments wherein each subfragment in the series is shorter than the preceding subfragment by 1–5 amino acid residues, preferably by a single amino acid residue. As each carboxy-terminal amino acid of the off-exchanged member is sequentially cleaved by the carboxypeptidase, the nitrogen which formed the slow-exchanging amide in the intact protein is converted to a rapidly-exchanging secondary amine, and any label at that nitrogen is lost from the protein within seconds, even at acidic pH. A difference in the molar quantity of label associated with any two sequential subfragments indicates that label is localized at the amide bond which differs between the two subfragments. Quantification of the amount of label at each labeled amide, for example by radioactivity or mass spectroscopy measurements, as a function of varying on or off-exchange periods yields the exchange rate for each residue of the labeled fragments. The positions of the residues are then correlated within the primary amino acid sequence of the member to yield the exchange rates of the amide hydrogens of the member.

Preferred acid stable carboxypeptidases for the controlled sequential degradation include carboxypeptidases P, Y, W and C, with carboxypeptidase P being particularly preferred.

4.2.2 Localisation of Amide Hydrogens by Mass Spectrometry

In a preferred embodiment, there is a lessened reliance on sequential degradation by peptidases. Instead, fragmentation occurs within a mass spectrometer. Typically, when a peptide is fragmented within a mass spectrometer employing conventional conditions, amide hydrogens become scrambled, i.e., exchange positions with other amide hydrogens within the same peptide. But by performing specialized forms of mass spectroscopy (ion-trap mass spectroscopy) and operating the mass spectrometer below a predetermined scrambling threshold fragmentation energy, such exchange can be avoided or minimised. (See, for example, Deng, Y., Pan, H., Smith, D. L. "Selective Isotope Labeling Demonstrates That Hydrogen Exchange at Individual Peptide Amide Linkages Can Be Determined by Collision-Induced Dissociation Mass Spectrometry", Journal of the American Chemical Society; 121(9), 1966–1967, (1999); D. L. Smith, Y. Dheng and Z. Zhang, "Probing the Non-covalent Structure of Proteins by Amide Hydrogen Exchange and Mass Spectrometry", Journal of Mass Spectrometry, 32, 135–146, (1997)). Unacceptable hydrogen scrambling on any given mass spectrometer can be identified by running the following cytochrome c control experiment.

The amount of heavy hydrogen incorporation in select subfragments of horse heart cytochrome c was determined as follows. Native horse heart cytochrome c (the polypeptide) was incubated in $D_2O$ for 10 seconds then acidified (pH 2.5) and cooled (0° C.) to quench isotope exchange. Pepsin was added to fragment the polypeptide into peptide cleavage products that are about 10 to 15 amino acids in length. The polypeptide cleavage products were analyzed by directly-coupled HPLC-electrospray ionization mass spectrometry to determine the mass of the peptide cleavage products. These masses were used with the appropriate standards to determine the deuterium level of each peptide cleavage product. Since rapidly exchanging deuterium in the side chains was back exchanged during the chromatographic step, the mass of the peptide cleavage product was a direct measure of the total number of deuteriums located at peptide amide linkages in the peptide cleavage product.

Equine cytochrome c (2 mM in $H_2O$/phosphate buffer, 5 mM, pH 7.0) was diluted 20 fold into $D_2O$/phosphate buffer (5 mM, pD 7.0) and incubated for 10 seconds to selectively label peptide amide linkages. Following incubation, the samples were acidified to quench isotope exchange, digested with pepsin and analyzed by LC MS (2 nmole injected). (Smith et al., 1997, *J. Mass. Spectrom.*, 32:135–146). Both MS and CID MS/MS analyses were performed with a Finnigan LCQ ion trap mass spectrometer. Analysis of peptide cleavage products from cytochrome c reference samples completely exchanged in $D_2O$ indicated that only 10% of the amide deuterium was lost during digestion, HPLC and MS analysis when the HPLC flow rate was 100 $\mu$L/min and the temperature of the ESI capillary was 150° C. Adjustments for deuterium loss during analysis were made as described in Zhang et al., 1993, *Protein Science*, 2:522–531.

Results for five representative peptide cleavage products derived from selectively labeled cytochrome c are presented in Table 1. Hydrogen exchange at each of these peptide cleavage product amide linkages is designated as fast (F) or slow (S), depending on whether the exchange rate constant was sufficiently slow ($k<30$ $h^{-1}$) to be determined by NMR. For the 10 second exposure to $D_2O$ used, the deuterium levels at individual amide linkages labeled S are expected to be less than 0.08. Deuterium levels expected for amide linkages labeled F cannot be predicted because exchange at these linkages was too fast to be measured by NMR. The deuterium levels at individual peptide amide linkages, determined from differences in the mass-to-charge (m/z) of CID subfragments, are presented in columns labeled b and y". Nearly all of the ions comprising the b and y" series of CID subfragment ions of these peptide cleavage products were sufficiently intense for accurate determination of their m/Z. Horizontal brackets in Table 1 indicate regions in which one or two subfragment ions were not found. For example, the pair of brackets in the b series of the peptide cleavage product that includes residues E4-G6 indicates that there is a total of 2.0 deuteriums in these three peptide linkages. Since labile deuterium located in the side chains was replaced with protium during HPLC, the deuterium detected by ESIMS was located at peptide amide linkages. (Bai et al., 1993, *Proteins: Struct. Funct. Genet.*, 17:75–86.)

TABLE 1

Deuterium levels found at individual peptide amide linkages in five peptide cleavage products (residues 1–10, 68–80, 95–104, 22–36, 83–94) of selectively labeled cytochrome c analyzed by CID MS/MS. Hydrogen exchange at these amide linkages is indicated as Fast (F) or slow (S), based on NMR analysis of cyctochrome c selectively labeled in a manner similar to Harrison et al. (Harrison et al., 1997, Int. J. Mass Spectrom. Ion Proc., 165:339–347.) The total deuterium in each peptide cleavage product was determined in a separate MS analysis of the doubly charged ion.

| Residue | NMR | b | y" |
|---|---|---|---|
| Residues 1–10 (total D:4.3) | | | |
| D2 | F | 0.9 | 1.1 |
| V3 | F | 0.9 | — |
| F4 | F | — | 1.6 |
| K5 | F | 2.0 | — |
| G6 | F | — | 0.1 |
| K7 | S | 0.3 | 1.1 |
| K8 | S | 0.0 | 0.0 |
| I9 | S | 0.1 | — |
| | | | 0.1 |
| F10 | S | 0.1 | — |
| Sum | | 4.3 | 4.0 |
| Residues 22–36 (total D:6.3) | | | |
| G23 | F | 1.1 | — |
| | | | 0.4 |
| G24 | F | 0.8 | — |
| K25 | F | — | 1.0 |
| | | 1.9 | |
| H26 | F | — | 2.7 |
| | | — | |
| K27 | F | 2.1 | — |
| T28 | F | — | 1.1 |
| G29 | S | 0.0 | 0.0 |
| P30 | | | |
| N31 | S | 0.0 | 0.0 |
| L32 | S | 0.0 | ? |
| H33 | S | 0.0 | ? |
| G34 | F | 0.0 | — |
| L35 | S | 0.0 | 1.1 |
| F36 | S | 0.0 | — |
| Sum | | 5.9 | 6.3 |
| Residues 68–80 (total D:4.2) | | | |
| E69 | S | 0.1 | 0.0 |
| N70 | S | 0.0 | 0.0 |
| P71 | | | |
| K72 | F | 0.9 | ? |
| K73 | S | 1.0 | 0.0 |
| Y74 | S | 0.0 | 0.9 |
| I75 | S | 0.0 | 0.0 |
| P76 | | | |
| G77 | F | 1.0 | — |

TABLE 1-continued

Deuterium levels found at individual peptide amide linkages in five peptide cleavage products (residues 1–10, 68–80, 95–104, 22–36, 83–94) of selectively labeled cytochrome c analyzed by CID MS/MS. Hydrogen exchange at these amide linkages is indicated as Fast (F) or slow (S), based on NMR analysis of cyctochrome c selectively labeled in a manner similar to Harrison et al. (Harrison et al., 1997, Int. J. Mass Spectrom. Ion Proc., 165:339–347.) The total deuterium in each peptide cleavage product was determined in a separate MS analysis of the doubly charged ion.

| Residue | NMR | b | y" |
|---|---|---|---|
| | | | 2.2 |
| T78 | F | 1.1 | — |
| K79 | S | 0.0 | 0.0 |
| M80 | S | 0.0 | 0.0 |
| Sum | | 4.1 | 3.1 |
| Residues 83–94 (total D:4.3) | | | |
| G84 | F | 1.1 | 0.2 |
| I85 | S | 0.0 | 0.0 |
| K86 | F | 0.8 | 0.1 |
| K87 | F | 1.3 | 0.9 |
| K88 | F | 0.8 | 1.2 |
| T89 | F | 0.3 | — |
| | | | 0.0 |
| E90 | S | 0.0 | — |
| R91 | S | 0.0 | 1.1 |
| E92 | S | — | — |
| D93 | S | 0.0 | 1.0 |
| L94 | S | 0.0 | — |
| Sum | | 4.3 | 4.5 |
| Residues 95–104 (total D:2.1) | | | |
| A96 | S | 0.0 | 0.1 |
| Y97 | S | 0.1 | 0.1 |
| L98 | S | 0.0 | 0.0 |
| K99 | S | 0.1 | 0.0 |
| K100 | S | 0.0 | 0.0 |
| A101 | S | 0.0 | 1.1 |
| T102 | S | 0.1 | 0.0 |
| N103 | F | 1.0 | — |
| | | | 1.1 |
| E104 | F | 1.0 | — |
| Sum | | 2.3 | 2.4 |

Results for the peptide cleavage product that includes residues 83–94 clearly demonstrate that deuterium levels at individual peptide amide linkages can be determined from the m/z of the b ions. All of the linkages designated S were found by CID MS/MS to have less than 0.1 deuterium. Since MS analysis of the intact peptide cleavage product showed that it contained 4.3±0.1 deuteriums, it follows that intramolecular migration of deuterium from deuterated linkages to nondeuterated linkages was negligible. The sum of deuterium levels at each amide linkage also indicated that this subfragment contained a total of 4.3±0.1 deuterium, thus satisfying the requirement for internal consistency. Although similar analysis of the y" ions often yields deuterium levels consistent with levels derived from b ions and NMR, there are several discrepancies, suggesting that H/D transfers occur in the process of forming y" ions. This phenomenon has been discussed previously. Anderegg et al., 1994, *J. Am. Soc. Mass. Spectrom.*, 5:425:433; Tang et al., 1993, *Anal. Chem.*, 65:2824–2834; Dongre et al., 1996, *J. Am. Chem. Soc.*, 118:8365–8374. Scrambling in the y" ions precludes use of the such ions for hydrogen exchange studies until the mechanisms of y" ion formation is further understood. The ability to prepare peptide reference standards with specific amide linkages labeled with deuterium, as described in the present study, will facilitate more detailed studies of these and related peptide fragmentation mechanisms.

Similar excellent correlation between deuterium levels expected, based on NMR, and deuterium levels found in b ions was found for the other four peptide cleavage products of cytochrome c. The only significant difference in deuterium levels found at S linkages by CID MS/MS and NMR is at Lys 73. Since the exchange rate at this residue is at the upper limit that could be measured for the NMR experimental conditions, and since the NMR crosspeak for this residue was unresolved from that for Lys 8, the uncertainty in the exchange rate at Lys 73 measured by NMR may be larger than expected. Although misassignment of peaks in the CID MS/MS spectrum is possible, it would not explain this discrepancy since the total deuterium in the entire peptide cleavage product was 4.2±0.1 and total number of fast exchanging linkages found by NMR was only 3. It follows that exchange at one of the linkages must be considerably faster than indicated by NMR.

In the foregoing control experiment, unacceptable hydrogen scrambling occurs when the amount of heavy hydrogen incorporation in the b ions generated from the five cytochrome c model peptide cleavage products, which have been prepared as described above, have an amount of heavy hydrogen incorporation that deviates more than ±0.2 from the values presented in Table 1. To achieve this type of agreement, it is expected that fewer than 10%, typically fewer than 5%, and preferably fewer than 1% of the hydrogen amides in the polypeptide of interest undergo an intermolecular or intramolecular shift during the mass spectroscopy fragmentation step.

One method of performing CID MS/MS below a hydrogen scrambling threshold is to use an "ion trap" spectrometer. As described in the cytochrome c control, above, Finnigan LCQ "ion-trap" mass spectrometer has successfully been used. Using the ion-trap spectrometer, the positions and quantities of amide heavy hydrogen within mass spectrometer-generated subfragments are measured without unacceptably scrambling the original location of the heavy hydrogen attached to the peptide amide linkages in the polypeptide. The CID mode of fragmentation that occurs in an ion-trap spectrometer is a highly controllable event, in terms of the fragmentation energy delivered to a peptide. This allows for the ability to operate the ion-trap spectrometer in a mode in which the fragmentation process is below a scrambling threshold. The methods of this invention can be extended to other mass spectrometers provided they are appropriately modulated to operate below the hydrogen scrambling threshold. Such mass spectrometers include ion cyclotron, triple quadrupole, MALDI, and electrospray time-of-flight mass spectrometers. For example, it is possible that the IonSpec (Irvine, Calif.) HiResMALDI® spectrometer may be adapted to operate below a hydrogen scrambling threshold.

If fragmentation by mass spectrometry is properly performed, the result is the generation of a series of subfragments similar in nature to the products produced by carboxypeptidases under conditions in which heavy hydrogen does not significantly interchange ("scramble") amongst the several amide hydrogen residues in the fragment. The weights of each subfragment are then determined within the mass spectrometer allowing identification of subfragments with attached heavy hydrogen labels. Such conditions can be achieved with the use of an "ion trap" form of mass spectrometer whereby the energy of fragmentation can be carefully controlled. Consequently the resulting spectrum identifies precisely which residue contains the heavy hydrogen.

4.2.3 Localisation of Amide Hydrogens by Other Methods and Summary

Alternatively, the controlled sequential degradation can be carried out using vapor phase pentafluoropropionic acid anhydride (PFPA) as described in Tsugita et al., 1992, Chemistry Letters pp. 235–238. Tsugita et al. dried 3 nmol of a dodecapeptide in a small test tube (6 mm×40 mm). The tube was then placed in a large test tube (13 mm×100 mm) which contained 100 µl of 10% PFPA in acetonitrile. The large tube was flame-sealed under vaccum at −30° C. The tube was maintained at reaction temperature of −18° C. for various time periods. After the reaction, the small tube was taken out and dried in vacuo. Two µl of dimethylformamide was added to the small tube and 1 µl of the product solution was mixed with an equal volume of glycerol as a matrix. The alternative embodiment of the present invention differs from that of Tsugita et al. in that the protein is kept at −35° C. for up to 3 hr. PFPA is then removed under vacuum, the subfragmented protein brought to 50 mM $PO_4$, pH 7.2 and analyzed by HPLC.

Those of skill in the art will recognize that in many instances the member will be of a sufficiently small size such that it need not be fragmented prior to the controlled sequential degradation. Thus, in an alternative embodiment, the exchanged members are optionally denatured under conditions of slowed hydrogen exchange and sequentially degraded as described above. Quantification of the amount of label at each amide as a function of exchange time yields the exchange rates for each residue of the unbound member.

Buffer conditions, protein concentrations and reagents, as well as automated procedures for carrying out each of the steps described above and additional optimal steps that can be used in conjunction with the invention are provided in U.S. Pat. No. 5,658,739, application Ser. No. 08/919,197, now issued as U.S. Pat. No. 6,291,189 B1, Sep. 18, 2001 or WO 97/41436, supra, which are hereby incorporated herein by reference.

Alternatively, the quantities and locations of the heavy hydrogens for each aliquot or time point can be determined using NMR under conditions of slowed hydrogen exchange. An advantage of NMR is that the labeled receptor or ligand can be placed in an aprotic solvent which greatly slows hydrogen exchange, for example, solutions composed of greater than 90% dimethylsulfoxide (DMSO), acetone, chloroform, and other similar organic solvents.

For these alternative methods, the whole receptor or ligand may be used, or optionally the receptor or ligand may first be denatured and fragmented into smaller pieces with, for example, chemicals such as CNBr or acid stable proteolytic enzymes, the labeled fragments identified and purified as previously described, and the locations and quantities of heavy hydrogens within each fragment determined via radioactivity measurement (tritium exchange), mass spectroscopy or NMR (deuterium). Of course, it will be understood that the denaturing, fragmenting, purification and analysis must be carried out under conditions of slowed hydrogen exchange.

In general, the foregoing techniques of localisation may be employed in concert, if so desired, once a receptor or ligand has been labelled. In one approach, optional preliminary fragmentation of the labelled receptor or ligand may take place if the molecule is large enough to require this, followed by an optional chromatographic separation of the fragmentation products. The fragmentation products may then themselves be subjected to further subfragmentation by collision induced mass spectroscopy, followed by examination of the resulting spectrum.

4.2.4 Localisation of Alkyl Hydrogens

As previously mentioned, the process of identifying the positions of labelled alkyl hydrogens is rendered more convenient by the fact that such hydrogens are not inherently labile and do not readily exchange with one another.

The general principle that the labelled receptor or ligand is degraded into fragments, usually comprising a manageable number of amino acid residues, may be extended to complete degradation to individual amino acids. For example, this might be a sequential localisation by enzymatic or chemical digestion. At this level one aims to locate the position of the alkyl hydrogen labels to within one amino acid residue. The principle may be extended further to identify the precise location of the heavy hydrogen on the amino acid by further degradation into "subfragments", by mass spectrometry.

4.3 Exchange Rates for the Bound State

Next, the exchange rates of the individual labile hydrogens of the member in its bound state to a binding partner are determined. Like the exchange rates of the unbound member, the exchange rates of the labile amide hydrogens of the bound member can be determined during on-exchange or off-exchange, or on and off exchange in sequence, using the previously-described methods. Correspondingly, the exchange rates of the labile alkyl hydrogens in the bound state may be determined by on-exchange.

For both amide and alkyl hydrogens the foregoing methods of localisation and quantification are employed for the bound state in order to deduce the quantities of hydrogens labelled on residues of interest.

4.3.1 Amide Hydrogen Exchange in the Bound State

In general, the conditions employed to effect amide hydrogen exchange on bound states of receptor ligand complexes are just the same as those that would be employed for the unbound states.

For example, for on-exchange the amide hydrogen exchange rates can be conveniently measured via NMR. In one embodiment, the member is contacted with its binding partner under conditions conducive to binding, forming a receptor-ligand complex. The receptor-ligand complex is then contacted with a solution of heavy hydrogen, again under conditions conducive to binding, and the rate of extinction of the individual amide hydrogen resonances monitored by $^1$H NMR. Since the amide hydrogens at the binding surface of the member are occluded from solvent by the presence of its binding partners, these amide hydrogens exchange reasonably slowly and have long-lived $^1$H NMR resonances.

In another embodiment, the receptor-ligand complex is contacted with tritiated water under conditions conducive to binding and the build-up rates of the individual amide hydrogen resonances monitored by $^3$H NMR.

For exchange rate measurements made during off-exchange, the member is first labeled with heavy hydrogen as previously described. Again, the member is on-exchanged for a period of time sufficient to substantially saturate the member. The labeled member is then contacted with its binding partner under conditions conducive to receptor-ligand binding. Upon binding, the solvent accessibilities of those member heavy hydrogens that interact with the binding partner are significantly diminished by the bound partner. Hence, the member heavy hydrogens that interact with the binding member are effectively "trapped" on the member.

The receptor-ligand complex is then dispensed into aliquots and each aliquot contacted with a solution of regular hydrogen under the same conditions used for formation of the receptor-ligand complex, and each aliquot off-exchanged for a different period of time. During the off-exchange incubation, the heavy hydrogens in solvent-accessible regions of the receptor-ligand complex off-exchange from the receptor, typically at the same rate as they originally on-exchanged.

However, the heavy hydrogens incorporated in the binding surface of the member off-exchange with normal hydrogens from the solvent at a significantly slower rate, since the bound binding partner decreases the solvent-accessibility of these residues. Again, off-exchange is quenched by placing the receptor-ligand complex under conditions of slowed hydrogen exchange, as previously described.

Typical time points for off-exchange are 1, 10, 100, $10^3$, $10^4$, $10^5$ sec., etc., but again optimal time points for a particular binding pair can be readily determined empirically.

Following the off-exchange incubation, the receptor-ligand complex of each aliquot is dissociated under conditions of slowed hydrogen exchange, the desired binding member recovered and the quantities and locations of heavy hydrogen labels within the amino acid sequence of the member determined for the various off-exchange intervals as described above. Again, suitable conditions for carrying out the off-exchange and optimal steps that can be used in conjunction with the methods are provided in U.S. Pat. No. 5,658,739, application Ser. No. 08/919,187, now issued as U.S. Pat. No. 6,291,189 B1, Sep. 18, 2001 and/or WO 97/41436, supra, and are incorporated herein by reference.

Once the exchange rates for each libable hydrogen of the binding member of interest have been obtained in both the bound and unbound states, the hot-spot residue for that particular member are identified according to Equation (II), supra. Those amino acids whose labile hydrogen has a $\Delta\Delta G$ that constitutes at least 10–20% of the overall free energy of binding of the complex are the hot-spot residues for that particular binding member.

While the "protection factors" for each residue of the binding member of interest can be determined according to the methods described above, in preferred embodiments the residues which constitute the binding surfaces of the member are first identified, preferably under native buffer conditions, and the protection factors of only those identified binding surface residues determined in order to identify the hot-spot residues. According to this preferred embodiment, the amino acid residues which constitute the binding surface of the member can be identified according to any available methods, including the methods described in U.S. Pat. No. 5,658,739, application Ser. No. 08/919,187, now issued as U.S. Pat. No. 6,291,189 B1, Sep. 18, 2001 and/or WO 97/41436; the methods of Clackson & Wells, 1995, supra, or from three-dimensional structural information for the receptor-ligand co-complex (where available).

In one convenient embodiment, the binding surface residues of the member are identified using the hydrogen exchange technique described in U.S. Pat. No. 5,658,739. During this process, a functionally-labeled member bearing heavy hydrogen labels only at residues which constitute the binding surface is generated, the functionally-labeled member is fragmented and the labeled fragments identified and isolated. Thus, by virtue of mapping the binding surface according to this method, conditions are obtained whereby fragments bearing labile hydrogens that reside within the binding surface of the member can be generated and isolated. Fragmenting the on-exchanged or off-exchanged members obtained with the methods of the invention under these same fragmentation conditions followed by purification under the previously-identified isolation condition permits only fragments bearing binding surface labile hydrogens to be selectively isolated and analyzed for labeled content.

Alternatively, if three-dimensional or other structure-function information is available that identifies which residues constitute the binding surface for the member or co-complex, conditions for selectively isolating fragments which bear these residues can be determined, and then only these fragments from the off-exchanged member are isolated and analyzed for label content.

If the receptor-ligand complex can be dissociated without disrupting the native structure of the binding member of interest, a functionally labeled member can be obtained as described in U.S. Pat. No. 5,658,739 and the exchange rates of the functionally labeled labile hydrogens in the unbound state obtained. The functionally-labeled complex is first dissociated under conditions of slowed hydrogen exchange, the desired binding member isolated, and the labile hydrogen exchange rates of the functionally-labeled labile hydrogens determined as previously described. For measurement of functionally labeled labile hydrogen exchange rates in the bound state, the functionally labeled co-complex is analyzed as previously described without first dissociating the complex.

Other methods for measuring protection factors of only those labile hydrogens which reside within the binding surface of the member which can be used in conjunction with the methods of the invention will be apparent to those of skill in the art.

4.3.2 Preferred Method of Obtaining Amide Exchange Protection Factors

In a preferred embodiment of the invention, the protection factors of only those labile hydrogens which reside in the binding surface of the member are conveniently obtained in a single experiment. In this embodiment, the member is on-exchanged as a function of time, typically by dispensing the member into a plurality of aliquots and on-exchanging the member in each aliquot for a different period of time, or by removing aliquots of on-exchanging member at defined time points. Typical on-exchange time points are 1, 10, $10^2$, $10^3$, $10^4$ and $10^5$ sec. Buffer conditions conducive to receptor-ligand binding should be used. The member in each aliquot is contacted with its binding partner and off-exchanged as a function of time, again typically by dispensing into aliquots. Each aliquot is off-exchanged for 0, 1, 10, 100 and $10^3$-times the on-exchange period. Preferably, the member is contacted with binding partner by passing it over a column of support-bound binding partner such as, e.g., binding partner-Sepharose. Following off-exchange, the reactions are quenched by changing the buffer conditions to conditions of slowed hydrogen exchange (typically pH 2.7 and 0° C.) and the amounts and locations of label determined for the member of interest as previously described.

Performing the experiment in this manner yields the following matrix of data points:

|  | On Exchange Time (sec.) | | | | | |
|---|---|---|---|---|---|---|
|  | 1 | 10 | 100 | $10^3$ | $10^4$ | $10^5$ |
| Off | 0 | 0 | 0 | 0 | 0 | 0 |
| Exchange | 1 | 10 | 100 | $10^3$ | $10^4$ | $10^5$ |
| Time | 10 | 100 | $10^3$ | $10^4$ | $10^5$ | $10^6$ |
| (sec.) | 100 | $10^3$ | $10^4$ | $10^5$ | $10^6$ | $10^7$ |
|  | $10^3$ | $10^4$ | $10^5$ | $10^6$ | $10^7$ | $10^8$ |

For each labile hydrogen in the member, plotting the quantity of label present for varying on-exchange times while holding the off-exchange time constant yields the exchange rates for each labile hydrogen in the unbound state. Plotting the quantity of label present for varying off-exchange times while holding the on-exchange time constant yields the exchange rates for each labile hydrogen in the bound state. The protection factors for each labile hydrogen, and their respective contributions to the free energy of binding, are determined as previously described.

Those of skill in the art will recognize that measuring protection factors according to this preferred method has several advantages. First, the matrix produces data redundancies which allow the quality of the measured exchange rates to be monitored. Data obtained for each off-exchange time (i.e., data obtained for diagonal matrix elements) yields exchange rates for each labile hydrogen of the member in the unbound state. Data obtained for each on-exchange time (i.e. data obtained for column matrix elements) yields exchange rates for each labile hydrogen of the member in the bound state. Stated another way, each matrix diagonal provides exchange rates for each member labile hydrogen in the unbound state and each matrix column provides exchange rates for each member labile hydrogen in the bound state. Thus, exchange rates across columns and diagonals can be compared as an internal check of the quality of the data.

Moreover, this matrix approach allows the exchange rates of labile hydrogens having different solvent accessibilities (and hence exchange rates) to be accurately determined. As previously discussed, labile hydrogens fall into several classes depending on their solvent accessibilities: rapidly exchanging, slowly exchanging and those there between. The exchange rates of these different classes can be obtained from the data set which, by virtue of the time points bracketed, produces the highest quality data for each particular class of labile hydrogen.

In addition, the matrix approach permits the protection factors of only those member residues of significance—those that reside in the binding surface—to be measured. This can be conveniently achieved by using a first off-exchange time point ($t_1$) greater than zero. Solvent accessible labile hydrogens, which do not reside in the binding surface, will exchange with solvent hydrogens and lose label during the period defined by $t_0$–$t_1$. The actual time used to off-exchange these uninteresting labile hydrogens prior to collecting time-dependent off-exchange data can be readily determined empirically. Typically an off-exchange pre-incubation on the order of from 1–5, 6, 7, 8, 9 or even as long as 10 seconds can be used to selectively unlabel labile hydrogens that do not reside in the binding surface of the member. By removing label from the rapidly exchanging solvent-accessible hydrogens, this method has the added advantage of allowing measurement of protection factors for labile hydrogens of interest under optimal conditions of signal-to-noise. Only those labile hydrogens of interest are labelled and are thus "seen" by the detection and quantification steps, thereby reducing background noise. Increases in signal to noise ratio over the two stage experiment of the order of 1,000:1 have been obtained.

While the methods of the invention have been described in terms of identifying hot-spot residues for one member of a receptor-ligand pair of interest, those of skill in the art will recognize that the methods can be used to identify hot-spot residues of both the ligand and receptor, either in individual experiments or simultaneously, so long as the receptor and ligand are each proteins of known amino acid sequence. Thus, the only requirement of the method is that the binding member for which hot-spot residues are desired be analyzable by hydrogen exchange, such as when the receptor or ligand is a protein of known or determinable amino acid sequence.

When hot-spot residues for both the receptor and ligand are desired, the exchange rates of the individual labile hydrogens for each binding member can be conveniently measured in a single experiment. For example, in instances when the NMR resonances of each binding member can be distinguished and assigned for the receptor-ligand complex, the exchange rates for the bound state can be conveniently measured in a single NMR on-exchange experiment.

Alternatively, if the NMR resonances of the complex cannot be resolved, the various off-exchange time points can be conveniently obtained in a single experiment by contacting a labeled receptor with a labeled ligand under conditions conducive to binding. After quenching off-exchange, the receptor-ligand complex can be dissociated and isolated under conditions of slowed hydrogen exchange and the exchange rates for the labile hydrogens of each binding member determined as previously described.

Preferably, the protection factors for each member of the binding pair are obtained in a single experiment using the data matrix approach described above.

4.3.3 Alkyl Hydrogen Exchange in the Bound State

Using similar principles as for amide hydrogen exchange, the method of labelling alkyl hydrogens for bound states is substantially the same as that for the unbound state. Only on-exchange in heavy hydrogen containing buffers need be employed. In order to obtain protection factors for alkyl hydrogens, one obtains only a timed series of on-exchanged samples of receptor bound to the ligand. From such measurements, exchange rates of receptor alkyl hydrogens in the bound state is deduced and protection factors calculated from the ratio for bound and unbound states. The same caveats with respect to the times for which radiation can take place as were identified for the unbound receptor or ligand apply here too.

It is worth noting that in the case that the ligand is a small organic molecule bound to a protein receptor, the alkyl hydrogen exchange labelling can label alkyl hydrogens on that ligand. Amide exchange labelling would, of course, only be able to provide direct information about the ligand contact regions if the ligand were a peptide or otherwise fortuitously contained an amide linkage.

4.3.4 General Conditions Employed for Hydrogen Exchange in the Bound State

For the various hydrogen exchange embodiments described herein that utilize radioactivity measurements and tritium labeling, the necessary level of tritiation (and hence the concentration of tritium in the buffer) is dependent on the total amount of protein available for analysis. For analysis of 1 mg protein, at least 10 Ci/ml is desirable; for 0.1 mg, 100 Ci/ml, and for 0.01 mg, 1000 Ci/ml (pure tritiated $H_2O$ is about 2500 Ci/ml.) For most applications, the tritiated water will be 50–500 Ci/ml. Without the use of these high specific activities, studies of proteins which are available in limited quantity would be much more difficult. Even higher specific activity (e.g., 500–1,500 Ci/ml) may be used in the invention, but radiation safety considerations necessitate performance of such on- and off-exchange procedures in specialized facilities, such as are available in the tritium laboratory provided by the National Tritium Facility, Lawrence Berkeley Laboratories, University of California, Berkeley.

It should be noted that with customary levels of tritium, only a small percentage of the binding protein molecules will be tritiated at any given exposed position. All that is required is that substantially each of the exposed labile hydrogen atoms be replaced in a number of the protein molecules that is detectable (by radiation counting).

For the various embodiments described herein utilizing deuterium labeling, on-exchange is preferably performed in 80–99% mole fraction deuterated water, more preferably 98% mole fraction deuterated water. The deuterated water may be optionally supplemented with, for example, 2% mole fraction tritiated water (e.g., 50 Ci/ml). This modified procedure labels the binding member with both deuterium and tritium such that either radioactivity measurements, mass spectrometry and/or NMR techniques can be used to identify and isolate labeled fragments and/or to localize and quantify the positions of the label within the polypeptide sequences of the member. Methods for using radioactivity and mass spectrometry measurements according to this modified embodiment are described in U.S. Pat. No. 5, 658,739, application Ser. No. 08/919,187 and/or WO 97/41436 supra, and are incorporated herein by reference.

4.4 Combined Application of Techniques

In general, it should be noted that the foregoing steps may be combined with one another in appropriate orders where convenient. For example, it may be appropriate to identify residues of interest (receptor-ligand binding hotspots) via amide hydrogen exchange labelling, and then perform focused studies on just such regions with alkyl hydrogen exchange labelling. Iterative combinations of the steps may likewise be employed in order to deduce both with convenience and specificity hot-spot residues.

4.5 Use of Hot Spot Information to Screen for Similar Binding Partners

In one extension of the foregoing discussion, it is apparent that the hydrogen exchange labelling and localisation techniques can be used to monitor changes in the contribution of a residue to binding energy in a series of mutant proteins or polypeptides.

In another aspect, the invention provides methods of identifying compounds, particularly small organic compounds, that mimic the binding of a known ligand for a receptor of interest, i.e., bind at or near the receptor hot-spot of a known ligand for the receptor of interest. As used herein, a ligand mimic is a compound which has a structure different from the ligand but which interacts with at least one receptor hot-spot residue of the receptor-ligand complex (hereinafter referred to as "$receptor_{R-L}$ hot-spot residues"). The greater the number of $receptor_{R-L}$ hot-spot residues interacted with by the compound, the closer the compound is considered to mimic the ligand. Preferably, the compound will interact with at least a majority, or even more, $receptor_{R-L}$ hot-spot residues. This approach represents a way of probing "mutations" of small molecules in a conceptually similar way to the process behind comparing mutations of the receptor.

The overall procedure behind this approach is that protection factor measurement is used within an iterative scheme comprising three parts. In the first part, protection factors are measured, thus identifying hot-spot residues; in the second, families of related molecules are obtained, for example by synthesis; and in the third part, those molecules are screened for activity against the receptor.

4.5.1 Iterative Discovery of Similar Binding Partners

According to the method of the invention, $receptor_{R-L}$ hot-spot residues for a receptor-ligand pair of interest are identified, typically under native conditions such as conditions of physiological temperature, pH, ionic strength and buffer. As will be recognized by those of skill in the art, the method is not limited to any particular method of identifying $receptor_{R-L}$ hot-spot residues. For example, the $receptor_{R-L}$ hot-spot residues can be identified according to previously-described methods of the invention, the site-directed mutagenesis methods of Clackson & Wells, 1995 supra, or any other method described in the art. Due to its ability to identify receptor$_{R-L}$ hot-spot residues for a receptor-ligand pair in its native conformation under native buffer conditions, the receptor$_{R-L}$ hot-spot residues are preferably identified by the methods of the invention previously described herein. However, any other technique that quantifies the contribution to binding free energy of individual receptor residues in a given receptor-ligand complex is sufficient to identify receptor$_{R-L}$ hot-spot amino acids for the screening steps discussed below. In this context, an appropriate choice of ligand is one that is known to be a natural binding partner for the receptor in question, though any other ligand that has been found to bind well can be used, as can, in principle, any mutated form of the receptor.

For the purposes of determining hot-spot residues for use in screening experiments, one embodiment comprises carrying out single time-point measurements on amide hydrogen exchange. This approach enables such sites as can be to be saturation labelled thereby quickly providing lower limits on their protection factors.

After the receptor$_{R-L}$ hot-spot residues have been identified, the receptor is screened with candidate compounds to select those compounds that, by virtue of their binding to the receptor, slow hydrogen exchange at one or more of the receptor$_{R-L}$ hot-spot residues. The candidate compounds can be any type of compound including biological compounds such as peptides, polypeptides, peptidomimetics, nucleic acids, carbohydrates and non-biological compounds such as small organic molecules. The compounds can be synthesized individually, or may be members of a library, such as a combinatorial library. As small organic molecules typically are preferred for pharmaceutical uses, these compounds are preferred for the screening steps described herein.

The candidate compounds can be screened directly for interaction with receptor$_{R-L}$ hot-spot residues according to the methods of the invention, or can be first "pre-screened" for a desired biological activity. For example, an initial screen can be performed by any conventional technique to assay for binding to the receptor, including non-selective binding assays and competitive inhibition of the binding of the native receptor-ligand complex. Other biological assays can also be used, and will be apparent to those of skill in the art, depending on the particular application.

Those candidate compounds that show some activity in the initial screen are then screened for interactions with the receptor$_{R-L}$ hot-spot residues. The compounds are screened for interactions with a receptor$_{R-L}$ hot-spot residue by receptor-candidate compound hot-spot screening, i.e., the hot-spot residues for the receptor-candidate compound complex are identified (hereinafter referred to as "receptor$_{R-C}$ hot-spot residues), typically using any of the previously described methods for identifying hot-spot residues. Those candidate compounds which produce a receptor$_{R-C}$ hot-spot residue identical to a receptor$_{R-L}$ hot-spot residue are considered to have interactions with a receptor$_{R-L}$ hot-spot residue. Preferably, each candidate compound is screened as a ligand in the hydrogen exchange techniques of the invention to identify the receptor$_{R-C}$ hot-spot residues for the receptor-candidate compound complex. Most preferably, the protection factors of the receptor residues that interact with the candidate compound are measured by deuterium or tritium exchange. Alternatively, other techniques can be used to determine the receptor$_{R-C}$ hot-spot residues for the receptor-candidate compound complex, including site-directed mutagenesis and NMR, as previously described.

Those candidate compounds that interact with the receptor in a manner most similar to a ligand of the receptor are selected as "mimics" of the ligand. The receptor$_{R-L}$ hot-spot residues are used to guide the selection of ligand "mimics" from the candidate compounds. Selection is based on the number of receptor$_{R-L}$ hot-spot residues the candidate compound interacts with, the magnitude of the protection factors of these particular receptor$_{R-L}$ hot-spot residues for the receptor-candidate complex and the number of other receptor residues the candidate compound interacts with. Those compounds from the pool that interact with the greatest number of receptor$_{R-L}$ hot-spot residues and the fewest number of other residues should be selected. Further distinction is provided by selecting those candidate compounds whose receptor$_{R-C}$ residue protection factors are similar in magnitude to the receptor$_{R-L}$ residue protection factor of the same residue.

In practice, in an initial round of screening any candidate compound that interacts with at least one receptor$_{R-L}$ hot-spot residues with any magnitude of protection factor is selected as a ligand mimic. This compound can then be modified, such as by acting as a core or lead structure for the creation of a combinatorial library, and the modified compounds screened according to the methods of the invention. In subsequent rounds of screening, selection parameters should include binding more receptor$_{R-L}$ hot-spot residues and providing protection factors closer in magnitude to those provided by the ligand. Eventually, compounds are isolated that closely mimic the ligand. Typically, these close ligand mimics will precisely interact with a majority, and preferably all, of the receptor$_{R-L}$ hot-spot residues.

Further selection criteria may include the ability of the candidate compounds to induce structural changes in the receptor, as identified by the ability of the candidate compound to reproduce portions of the ligand-impressed thermodynamic fingerprint known to report such structural changes. In addition, the compounds can also be tested for their ability to function in vitro and/or in vivo as antagonists of the action of the ligand on the receptor.

The information learned from the above screening methods may be used in conjunction with any other available data to guide the identification of compounds that precisely target the thermodynamic hot-spots of a given receptor-ligand complex. The methods can be used iteratively with successive rounds of hot-spot screening. In addition, other information, including three-dimensional structures of the receptor, ligand or the receptor-ligand complex, where available, can be used to guide the methods. However, it will be recognized that success of the methods does not rely on the availability of such information—it can merely be used to enhance the methods when available.

4.5.2 Application to Combinatorial Chemistry

A candidate compound found to satisfy part of the thermodynamic fingerprint of the receptor-ligand interaction as determined by hot-spot screening is in turn employed as the lead structure for the generation of a new combinatorial library of compounds from which additional compounds can be selected that act as ligand mimics. A combinatorial library, is really just a library of small molecule mutants. One approach is to have every member of such a library consist of this identified compound decorated with additional structural features in a combinatorial manner, followed by selection of compounds that impress in the receptor not only the ligand's hot-spot fingerprint, but that also induce additional desired fingerprint interactions. Successive rounds of such combinatorial library generation and selection are performed until the desired level of affinity and/or specificity for the receptor is achieved. Progressive acquisition of the highest protection factor contact surface targets in each round will result in isolation of compounds that, for their size, optimally interact with the largest number of energetically important receptor residues.

Promising compounds that target important receptor residues, but that also have an excessive number of irrelevant interactions with the receptor can be optimized by producing a combinatorial library that contains smaller versions of the compound with various portions of the compound deleted and selecting compounds that retain reactivity with thermodynamically important receptor residues but that no longer interact with unimportant receptor residues. Similarly, efforts to improve other properties of the compound, such as oral bioavailability, protein binding, and plasma half-life can proceed with the knowledge of which portions of the compound can be altered without a likely effect on the desired thermodynamic fingerprint. The concept of making purposeful modifications to an existing lead and assessing the results of such structural changes on functional activity is known in the art. It is an object of this invention to supplement the art by independently and simultaneously assessing the interactions of a compound with each residue of the receptor, or each residue of the receptor-ligand binding surface. Presently, the art is incapable of providing such detailed thermodynamic binding information absent solving the three-dimensional structure of the co-complex, which is a laborious, expensive undertaking. Even then, such detailed thermodynamic information can oftentimes only be inferred.

4.5.3 Application to Agonist Identification

The invention also encompasses an approach to identify compounds, particularly small organic compounds, with agonist activity from a pool of candidate compounds. A ligand's agonist activity towards a receptor is usually mediated by binding-induced oligomerization or conformational change in it's cellular receptor.

The slowing of labile hydrogen exchange induced in a receptor by agonist ligand binding can arise by three distinct mechanisms:
(i) slowing of labile hydrogen exchange in residues that are in the receptor-ligand binding surface;
(ii) slowing of labile hydrogen exchange because particular residues participate in conformational changes as a consequence of the binding event (and therefore experience changes in their solvent accessibilities); and
(iii) slowing of labile hydrogen exchange in certain residues that participate in binding-induced receptor sub-unit oligomerization (and therefore experience decreased solvent accessibility because of these new subunit associations). If detailed information exists concerning the nature of the structure of the receptor-ligand complex, the simple inspection of such models in conjunction with the obtained protection factors of the residue allows discernment between amino acid residues in each of these three classes. The result is: (1) identification of residues that participate in receptor-ligand binding (and subsequent localization of receptor-ligand hot-spots); (2) identification of receptor residues that participate in conformational changes within the receptor; and (3) identification of oligomerization surface(s) of receptor sub-units.

If such structural information is unavailable, the receptor residues in the receptor-ligand binding surface can be identified and discerned from amino acid residues slowed from conformational change or oligomerization by labeling the ligand with heavy hydrogen according to the methods previously described, forming a receptor-ligand complex, and identifying those receptor residues that become labeled by transfer from the labeled ligand. Methods for carrying out such label-transfer experiments are described in U.S. Pat. No. 5,658,739, application Ser. No. 08/919,187, now issued as U.S. Pat. No. 6,291,189 B1, Sep. 18, 2001 and WO 97/41436, supra, and are incorporated herein by reference. Since this transfer occurs principally at the binding surface, the hot-spot residues on the receptor binding surface can be distinguished from residues which exhibit changes in hydrogen exchange rates due to conformational changes and/or oligomerization. Those receptor residues whose hydrogen exchange rates change due to conformational changes and/or ligand-induced receptor oligomerization can be monitored in the methods of this invention to screen candidate compounds for potential agonist activity.

To identify compounds which exhibit agonist activity, a candidate compound is screened with the receptor as a ligand using the hydrogen exchange techniques described herein. Those candidate compounds that interact with at least one receptor residue belonging to class (ii) or (iii), supra, as determined by having a protection factor of at 1, are identified as having potential agonist activity, which is confirmed using standard biological assays.

Alternatively, a pool of candidate compounds is first screened with the receptor to identify those candidate compounds that possess agonist activity. The identified compounds are then screened with the receptor using the hydrogen exchange techniques described herein to identify those compounds that interact with at least one receptor residue belonging to class (ii) or (iii), supra. Interative rounds of screening can be used to identify compounds which closely mimic the agonist, as determined by identifying compounds that interact with a majority of the class (ii) or class (iii) receptor residues, and optionally which induce protection factors substantially equal in magnitude at these residues to that induced by the agonist.

As those of skill in the art will appreciate, the methods of the invention are not limited to identifying compounds which mimic a receptor's natural ligand. In many instances, other ligands which bind a receptor are known. These ligands can be used in the methods of the invention to identify new ligands which mimic their binding and/or activity.

The foregoing written specification is sufficient to enable one of skill in the art to practice the invention. Various modifications of the above-described modes for carrying out the invention which are obvious to those of skill in the art are intended to be within the scope of the appended claims.

All cited references are hereby incorporated by reference in their entireties for all purposes.

What is claimed is:

1. A method for identifying a hot-spot residue of a member of a receptor-ligand complex, comprising:
    (a) obtaining a protection factor of an alkyl hydrogen on at least one individual amino acid residue of the member;
    (b) determining from said protection factor, the contribution of said at least one individual amino acid residue to an overall free energy of binding of the complex; and
    (c) identifying said at least one amino acid residue as a hot-spot residue if said contribution is at least about 10% of said overall free energy of binding.

2. The method of claim 1 wherein said at least one individual amino acid residue is in a binding surface of the member.

3. The method of claim 1 further comprising identifying additional amino acid residues as hot-spot residues that contribute about 20–30% in sum to said overall free energy of binding of the complex.

4. The method of claim 1 further comprising identifying additional amino acid residues as hot-spot residues that contribute about 40% in sum to said overall free energy of binding of the complex.

5. The method of claim 1, wherein said obtaining comprises:
(i) measuring a first hydrogen exchange rate of said alkyl hydrogen when the member is in an unbound state;
(ii) measuring a second hydrogen exchange rate of said alkyl hydrogen when the member is in a bound state; and
(iii) taking the ratio of said first hydrogen exchange rate with said second hydrogen exchange rate.

6. The method of claim 5 wherein said measuring a first hydrogen exchange rate of said alkyl hydrogen comprises:
contacting the member with a source of heavy hydrogen for varying "on-exchange" periods under conditions wherein alkyl hydrogens in the member which are accessible to solvent exchange with heavy hydrogen, thereby producing a labeled member;
for each of said "on-exchange" periods, localizing and quantifying an amount of heavy hydrogen label associated with said alkyl hydrogen of said at least one individual amino acid residue of the member; and
determining said hydrogen exchange rate for said alkyl hydrogen of said at least one individual member residue from said amount of heavy hydrogen label associated with said residue as a function of said varying "on-exchange" periods.

7. The method of claim 6 wherein said localizing and quantifying comprises:
fragmenting said labeled member into a plurality of fragments;
identifying which of said plurality of fragments are labeled with heavy hydrogen;
progressively degrading each of said plurality of fragments which is labeled with heavy hydrogen to obtain a series of subfragments, wherein each subfragment of said series is composed of about 1–5 fewer amino acid residues than the preceding subfragment in the series;
measuring an amount of heavy hydrogen associated with each subfragment; and
correlating said amount of heavy hydrogen associated with each subfragment with an amino acid sequence of said fragment from which said subfragment was generated, thereby localizing the position of said alkyl hydrogen to a resolution of about 1–5 amino acid residues.

8. The method of claim 7 in which said heavy hydrogen label is tritium and said identifying and said measuring are carried out by radioactivity measurements.

9. The method of claim 7 in which said heavy hydrogen label is deuterium and said identifying and said measuring are carried out by NMR spectroscopy.

10. The method of claim 7 further including the step of separating said plurality of fragments prior to determining which of said plurality of fragments are labeled with heavy hydrogen.

11. The method of claim 7 in which said progressively degrading comprises contacting said fragments which are labelled with heavy hydrogen with an acid resistant carboxypeptidase selected from the group consisting of carboxypeptidase P, carboxypeptidase Y, carboxypeptidase W and carboxypeptidase C.

12. The method of claim 7 in which said fragmenting said labeled member comprises contacting said labeled member with an acid stable proteolytic enzyme selected from the group consisting of: pepsin, Newlase, Aspergillus proteases, and protease type XIII.

13. The method of claim 7 in which, any disulfide bridges in said labeled member are disrupted under conditions of slow hydrogen exchange prior to fragmenting or progressively degrading.

14. The method of claim 7 wherein prior to fragmenting or subfragmenting, said labeled member is denatured.

15. The method of claim 14 in which said solvent further includes about 2–4 M guanidine thiocyanate.

16. The method of claim 5 wherein said measuring a second hydrogen exchange rate of said alkyl hydrogen comprises:
contacting the member with a source of heavy hydrogen for varying "on-exchange" periods sufficient for solvent-accessible alkyl hydrogens of the member to exchange with, and be substantially replaced by, heavy hydrogens of the solvent thereby producing a labelled member;
contacting said labeled member with a binding partner under conditions wherein the heavy hydrogen labels are substantially retained and wherein the member binds said partner so as to form a receptor-ligand complex;
for each of said "on-exchange" periods, localizing and quantifying an amount of heavy hydrogen label associated with said alkyl hydrogen of said at least one individual amino acid residues of the member; and
determining said exchange rate of said alkyl hydrogen of said at least one individual member residue from said amount of heavy hydrogen label associated with said residue as a function of said varying "on-exchange" periods.

17. The method of claim 16 wherein said localizing and quantifying comprises:
dissociating said receptor-ligand complex and recovering the on-exchanged member of interest;
fragmenting said labeled member into a plurality of fragments;
identifying which of said plurality of fragments are labeled with heavy hydrogen;
progressively degrading, each of said plurality of fragments which is labeled with heavy hydrogen to obtain a series of subfragments, wherein each subfragment of said series is composed of about 1–5 fewer amino acid residues than the preceding subfragment in the series;
measuring an amount of heavy hydrogen associated with each subfragment; and
correlating said amount of heavy hydrogen associated with each subfragment with an amino acid sequence of said fragment from which said subfragments was generated, thereby localizing the position of said alkyl hydrogen to a resolution about 1–5 amino acid residues.

18. The method of claim 17 in which said heavy hydrogen label is tritium and said identifying and said measuring are carried out by radioactivity measurements.

19. The method of claim 17 in which said heavy hydrogen label is deuterium and said identifying and said measuring are carried out by measuring the mass of the fragment or subfragment.

20. The method of claim 17 further including the step of separating said plurality of fragments prior to determining which of said plurality of fragments are labeled with heavy hydrogen.

21. The method of claim 17 in which said progressively degrading comprises contacting said fragments which are labelled with heavy hydrogen with an acid resistant carboxypeptidase selected from the group consisting of carboxypeptidase P, carboxypeptidase Y, carboxypeptidase W and carboxypeptidase C.

22. The method of claim 17 in which said fragmenting said labeled member comprises contacting said labeled member with an acid stable proteolytic enzyme selected from the group consisting of: pepsin, Newlase, Aspergillus proteases, and protease type XIII.

23. The method of claim 17 in which any disulfide bridges in said labeled member are disrupted under conditions of slow hydrogen exchange prior to fragmenting or progressively degrading.

24. The method of claim 17 wherein prior to fragmenting or subfragmenting, said labeled member is denatured.

25. The method of claim 24 in which said solvent further includes about 2–4 M guanidine thiocyanate.

26. The method of claim 5 wherein said exchange rate of said alkyl hydrogen of said at least one individual amino acid residue of the member in the unbound state is determined by deuterium or tritium exchange NMR.

27. The method of claim 5 wherein said exchange rate of said alkyl hydrogen of said at least one individual amino acid residue of the member in the bound state is determined by deuterium or tritium exchange NMR.

28. The method of claim 7, in which the presence or amount of heavy hydrogen on a fragment or subfragment is determined by measuring the mass of the fragment or subfragment by mass spectrometry.

29. The method of claim 7 in which the progressively degrading of the labeled fragments comprises a combination of enzymatic fragmentation and collision induced mass spectrometry.

30. A method of identifying a compound that binds to a receptor at hot-spot residues, comprising:
 (a) identifying, for the receptor, at least one hot-spot residue to which a known ligand binds, by:
  (i) obtaining a protection factor of a hydrogen on at least one individual amino acid residue of the receptor;
  (ii) determining from said protection factor, the contribution of said at least one individual amino acid residue to an overall free energy of binding of a complex between said known ligand and the receptor; and
  (iii) identifying said at least one amino acid residue as a hot-spot residue if said contribution is at least about 10% of said overall free energy of binding between said known ligand and the receptor; and
 (b) selecting from a pool of candidate compounds that has been screened against the receptor, a compound that binds to said at least one hot-spot residue.

31. The method of claim 30 wherein said pool of candidate compounds is screened for binding to the receptor and a compound that binds to the receptor is screened for binding to receptor hot-spot residues.

32. The method of claim 30 in which the receptor hot-spot residues are identified by the technique of site-directed mutagenesis.

33. A method of identifying a compound which acts as an agonist for a receptor, comprising:
 (a) identifying for a receptor-agonist pair those receptor residues which participate in receptor-agonist binding, receptor conformational changes as a consequence of a receptor-agonist binding event or receptor subunit oligomerization, by:
  (i) obtaining a protection factor of a hydrogen on at least one individual amino acid residue of the receptor;
  (ii) determining from said protection factor, the contribution of said at least one individual amino acid residue to an overall free energy of binding of said receptor-agonist pair; and
  (iii) identifying said at least one amino acid residue as a hot-spot residue if said contribution is at least about 10% of said overall free energy of binding of said receptor-agonist pair;
 (b) screening a pool of candidate compounds against the receptor; and
 (c) selecting from said pool of candidate compounds those compounds that interact with at least one receptor residue which participates in receptor conformational changes as a consequence of a receptor-agonist binding event or receptor subunit oligomerization, thereby identifying an agonist for the receptor.

34. The method of claim 30 wherein said hydrogen is an amide hydrogen on a peptide link between two adjacent amino acid residues of the member.

35. The method of claim 30 wherein said hydrogen is an alkyl hydrogen on an individual amino acid residue of the member.

36. The method of claim 30 wherein said hydrogen is an amide hydrogen on a peptide link between two adjacent amino acid residues of the member.

37. The method of claim 30 wherein said hydrogen is an alkyl hydrogen on an individual amino acid residue of the member.

38. The method of claim 6 wherein said contacting comprises reacting said member with a solution of hydrogen atom abstractor.

39. The method of claim 38 wherein said hydrogen atom abstractor is a hydroxyl radical.

40. The method of claim 39 wherein said hydroxyl radical is generated by application of radiolysis.

41. The method of claim 40 wherein said radiolysis involves application of γ-rays.

42. The method of claim 6 wherein said source of heavy hydrogen is heavy water.

43. The method of claim 42 wherein said heavy water contains up to 80% mole fraction of deuterium.

44. The method of claim 40 wherein, prior to said application of radiolysis, dissolved oxygen gas is removed from said solution by bubbling dinitrogen gas through said solution.

45. The method of claim 38 wherein said solution additionally comprises a heavy hydrogen donor.

46. The method of claim 45 wherein said heavy hydrogen donor is dithiotreitol.

47. The method of claim 4 wherein said solution has a pH of less than 9.0.

48. The method of claim 6 wherein said localizing and quantifying comprises:
 completely degrading said labeled member into a plurality of individual amino acids;
 identifying which of said plurality of amino acids are labeled with heavy hydrogen;
 measuring an amount of heavy hydrogen associated with each amino acid; and
 correlating said amount of heavy hydrogen associated with each amino acid with an amino acid sequence of said fragment from which said amino acid was generated, thereby localizing the position of said alkyl hydrogen that had been labeled with heavy hydrogen to one amino acid residue.

49. The method of claim 48 wherein said completely degrading is accomplished by used of an enzyme.

50. The method of claim 16 wherein said contacting comprises reacting said member with a solution of hydrogen atom abstractor.

51. The method of claim 50 wherein said hydrogen atom abstractor is a hydroxyl radical.

52. The method of claim 51 wherein said hydroxyl radical is generated by application of radiolysis.

53. The method of claim 52 wherein said radiolysis involves application of γ-rays.

54. The method of claim 16 wherein said source of heavy hydrogen is heavy water.

55. The method of claim 54 wherein said heavy water contains up to 80% mole fraction of deuterium.

56. The method of claim 52 wherein, prior to said application of radiolysis, dissolved oxygen gas is removed from said solution by bubbling dinitrogen gas through said solution.

57. The method of claim 50 wherein said solution additionally comprises a heavy hydrogen donor.

58. The method of claim 57 wherein said heavy hydrogen donor is dithiotreitol.

59. The method of claim 58 wherein said solution has a pH of less than 9.0.

60. The method of claim 16 wherein said localizing and quantifying comprises:

completely degrading said labeled member into a plurality of individual amino acids;

identifying which of said plurality of amino acids are labeled with heavy hydrogen;

measuring an amount of heavy hydrogen associated with each amino acid; and correlating said amount of heavy hydrogen associated with each amino acid with an amino acid sequence of said fragment from which said amino acid was generated, thereby localizing the position of said alkyl hydrogen that had been labeled with heavy hydrogen to within one amino acid residue.

61. The method of claim 60 wherein said completely degrading is accomplished by use of an enzyme.

* * * * *

UNITED STATES PATENT AND TRADEMARK OFFICE
CERTIFICATE OF CORRECTION

PATENT NO. : 6,599 707 B1  
DATED : July 29, 2003  
INVENTOR(S) : Virgil L. Woods, Jr.

It is certified that error appears in the above-identified patent and that said Letters Patent is hereby corrected as shown below:

Column 34,  
Lines 26 and 29, change "30" to -- 33 --.

Signed and Sealed this

Ninth Day of August, 2005

JON W. DUDAS  
*Director of the United States Patent and Trademark Office*